US012678194B2

(12) United States Patent
Katayama

(10) Patent No.: US 12,678,194 B2
(45) Date of Patent: Jul. 14, 2026

(54) PUNCTURE DEVICE, PUNCTURE SYSTEM, OPERATION METHOD OF PUNCTURE DEVICE, AND USAGE METHOD OF GUIDEWIRE

(71) Applicant: OLYMPUS MEDICAL SYSTEMS CORP., Tokyo (JP)

(72) Inventor: Tomofumi Katayama, Kunitachi (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 604 days.

(21) Appl. No.: 18/172,704

(22) Filed: Feb. 22, 2023

(65) Prior Publication Data

US 2023/0310030 A1     Oct. 5, 2023

Related U.S. Application Data

(60) Provisional application No. 63/363,081, filed on Apr. 15, 2022, provisional application No. 63/268,556, filed on Feb. 25, 2022.

(51) Int. Cl.
| | |
|---|---|
| *A61B 17/34* | (2006.01) |
| *A61B 8/12* | (2006.01) |
| *A61M 25/01* | (2006.01) |
| *A61B 10/04* | (2006.01) |
| *A61B 17/00* | (2006.01) |
| *A61M 25/09* | (2006.01) |

(52) U.S. Cl.
CPC ............ *A61B 17/3478* (2013.01); *A61B 8/12* (2013.01); *A61M 25/0108* (2013.01); *A61B 2010/045* (2013.01); *A61B 2017/0034* (2013.01); *A61B 2017/3413* (2013.01); *A61M 25/09* (2013.01)

(58) Field of Classification Search
CPC . A61B 17/3478; A61B 8/12; A61B 2010/045; A61B 2017/0034; A61B 2017/3413; A61B 8/445; A61B 2017/22038; A61B 2090/0801; A61M 25/0108; A61M 25/09; A61M 25/09041; A61M 25/065
See application file for complete search history.

(56) References Cited

U.S. PATENT DOCUMENTS

| | | | | |
|---|---|---|---|---|
| 6,425,887 B1 * | 7/2002 | McGuckin | ......... | A61B 17/1671 |
| | | | | 604/272 |
| 2006/0276873 A1 * | 12/2006 | Sato | .................... | A61B 17/3468 |
| | | | | 623/1.11 |
| 2016/0157839 A1 | 6/2016 | Eckerline et al. | | |

FOREIGN PATENT DOCUMENTS

WO     WO-2020016981 A1 *   1/2020   ........ A61M 25/0643

* cited by examiner

*Primary Examiner* — Richard G Louis
(74) *Attorney, Agent, or Firm* — Schwegman Lundberg & Woessner, P.A.

(57) ABSTRACT

A puncture device comprises an elongate sheath, defining a longitudinal axis direction; a needle tube, carried in the sheath, the needle tube configured to be movable in the longitudinal axis direction; a needle slider, connected to the needle tube; an inner tube, carried in the needle tube, the inner tube defining a lumen configured to receive a guide wire; a tube slider, connected to the inner tube, the tube slider configured to support the inner tube such that the inner tube is movable in the longitudinal axis direction; and a locking member, configured to lock the needle slider relative to the tube slider in a first state and in a second state, wherein: in the first state, a distal end of the inner tube is positioned in the needle tube; and in the second state, the distal end of the inner tube is positioned to protrude from the needle tube.

12 Claims, 21 Drawing Sheets

FIG. 16C

PUNCTURE DEVICE, PUNCTURE SYSTEM, OPERATION METHOD OF PUNCTURE DEVICE, AND USAGE METHOD OF GUIDEWIRE

CROSS-REFERENCE TO RELATED APPLICATIONS

This application is based upon and claims the benefit of priority to U.S. Provisional Application Ser. No. 63/268,556, filed on Feb. 25, 2022, and U.S. Provisional Application Ser. No. 63/363,081, filed on Apr. 15, 2022, the entire contents of which is incorporated herein by reference.

TECHNICAL FIELD

The present disclosure relates to a puncture device, a puncture system, an operation method of a puncture device, and a usage method of a guidewire.

BACKGROUND

Examining and treating lumens such as the bile ducts and the pancreatic ducts can include using an ultrasonic endoscope. According to the technology, for example, after a tube is inserted into the lumen, the confirmation is performed by injecting a contrast agent and performing the radiography imaging. After the radiography imaging, a guidewire is introduced into the lumen to proceed with the treatment.

Puncturing the tissue by a puncture device and then introducing a guidewire into the body via an inner hole of a needle tube punctured into the tissue In order to prevent damage to the guide wire due to the edge of the distal end of the needle tube, a protective tube (inner tube) protruding from the distal end of the needle tube is inserted into the inner hole of the needle tube, and the guide wire is protruded from the inner hole of the protective tube. At the time of puncturing the lumen with the needle tube, the protective tube is accommodated in the needle tube, and when the guide wire is protruded from the needle tube, the protective tube protrudes from the needle tube.

SUMMARY

The present disclosure is made in consideration of the above-described circumstances, and a goal of the present disclosure can be to provide a puncture device, a puncture system, an operation method of a puncture device, and a usage method of a guide wire to help inhibit or prevent unintentional advancement of a tube through which a guide wire is insertable.

Examples of Means for Solving the Technical Problems

In order to solve the above-described problems, the present disclosure proposes the following techniques.

A puncture device according to a first aspect of the present disclosure, includes an elongate sheath including or defining a longitudinal axis; a needle tube carried or disposed in the sheath to be advanceable and retractable along the longitudinal axis; a needle slider connected to the needle tube and configured to advance and retract the needle tube; an inner tube disposed in the sheath to be advanceable and retractable along the longitudinal axis, the inner tube including or defining a lumen through which a guide wire is inserted to be advanceable and retractable along the longitudinal axis;

a tube slider connected to the inner tube, supported to be movable in a direction along the longitudinal with respect to the needle slider, and configured to advance and retract the inner tube; and a locking portion configured to lock positions of the needle slider and the tube slider in the direction along the longitudinal axis in each of an first state in which a distal end of the inner tube is accommodated in the needle tube and a second state in which the distal end of the inner tube is protruded from the needle tube.

BRIEF DESCRIPTION OF THE DRAWINGS

FIG. 16C is a cross-sectional view showing an example of a protrusion state in which the distal end of the protective tube protrudes from the needle tube.

DETAILS OF EMBODIMENTS

Figure 1:
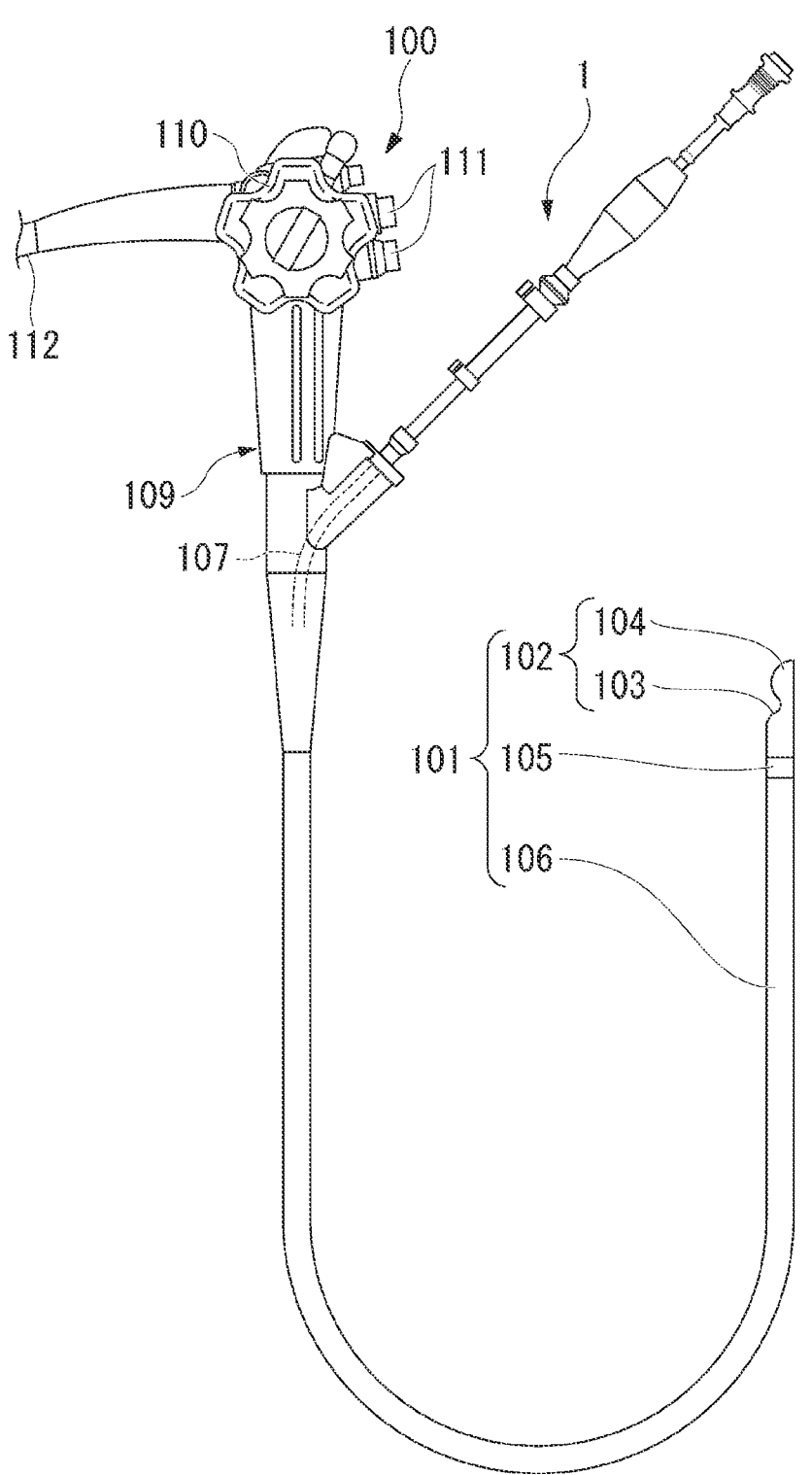
FIG. 1 is a view showing an example of a state in which a puncture device according to the present disclosure is attached to an ultrasonic endoscope.

A puncture device according to each embodiment described below may be used in a biopsy in combination with an ultrasonic endoscope 100 shown in FIG. 1, as an example of a biopsy system. FIG. 1 is a view showing a state in which the puncture device according to the present disclosure is attached to an ultrasonic endoscope.

First, an example of the endoscope used together with the puncture device 1 according to the present embodiment will be described. The configuration of the endoscope that may be used together with the puncture device 1 according to the present embodiment is not particularly limited.

The ultrasonic endoscope 100 includes at least an insertion portion 101 sized and shaped and otherwise configured to be inserted into the body such as a human subject from a distal end, an operation portion 109 attached to a proximal end of the insertion portion 101, and a universal cord 112 including an end that is connected to a lateral portion of the operation portion 109.

The insertion portion 101, a distal end rigid portion 102, a bending portion 105, and a flexible tubular portion 106 is provided from the distal end side in this order.

The distal end rigid portion 102 includes an optical imaging mechanism 103 for performing optical observation, and an ultrasonic scanning or other ultrasonic imaging mechanism 104 for performing ultrasonic observation.

The Optical imaging mechanism 103 includes an imaging optical system in which a visual filed is directed obliquely forward of the distal end rigid portion 102, an image sensor such as a CCD or CMOS configured to detect an image of the subject incident through the imaging optical system, and various configurations such as a controller circuitry such as a CPU (Central Processing Unit) or the like that are not shown and configured to control the operations of the image sensor, to process image, or both.

The ultrasonic scanning mechanism (probe) 104 includes an ultrasonic vibrator (not shown) that emits and receives ultrasonic waves. The ultrasonic scanning mechanism 104 receives the reflected wave reflected in response to the ultrasonic wave emitted by the ultrasonic vibrator reaches the observation object, and outputs an electrical, optical, or other signal based on the ultrasonic wave received by the ultrasonic vibrator via the ultrasonic observation unit 115. The ultrasonic scanning mechanism 104 can be used to acquire an ultrasonic image of a tissue as a biopsy target and to acquire an ultrasonic image of the needle tube 3 during the process of the biopsy procedure.

The bending portion 105 can be formed in a cylindrical cross-sectional shape. By pulling a shape-memory or other angle wire (not shown) such as which can be fixed to the distal end of the bending portion 105 and extending to the operation portion 109 at the operation portion 109, it is possible to make the bending portion 105 to bend to a predetermined direction.

For example, when a treatment with respect to a respiratory organ is performed, it may be preferable to use an endoscope having an insertion portion with a narrow outer diameter while capable of being bent in two directions, and when a treatment with respect to a digestive organ is performed, it may be preferable to use an endoscope having a thick outer diameter while capable of being bent in four directions to have a high degree of operation freedom.

The flexible tubular portion 106 is a cylindrical member fixed to the bending portion 105. The flexible tubular portion 106 is flexibly formed so as to guide the distal end rigid portion 102 to a desired position in the lumen tissue or in the body cavity.

Inside each of the bending portion 105 and the flexible tubular portion 106, a lumen, conduit, or working channel 107 through which the puncture device 1 is inserted and a further lumen, conduit, or auxiliary channel for performing air supply, water supply, suction, and the like are provided.

One end of the channel 107 is opened in the vicinity of the distal end rigid portion 102, the other end of the channel 107 is opened to the lateral surface at the distal end side of the operation unit 109. A proximal end cap 108 formed in a flange shape is fixed to the other end of the channel 107. A puncture device 1 to be used together with the ultrasonic endoscope 100 may be fixed to the proximal end cap 108.

The operation unit 109 as shown in FIG. 1 has an outer surface formed so as to be held by a surgeon by hand who uses the ultrasonic endoscope 100. Furthermore, the operation unit 109 includes a bending operation mechanism 110 such as configured to pull the angle wire to bend the bending portion 105, and one or a plurality of switches 111 configured to perform such as the air supply, the water supply, or the suction through the conduit.

Next, a configuration according to each embodiment of the puncture device 1 according to the present disclosure will be described.

First Embodiment

[Configuration of Puncture Device 1]

The puncture device 1 according to the first embodiment of the present disclosure will be described below with reference to FIG. 2 to FIG. 11.

Figure 2:
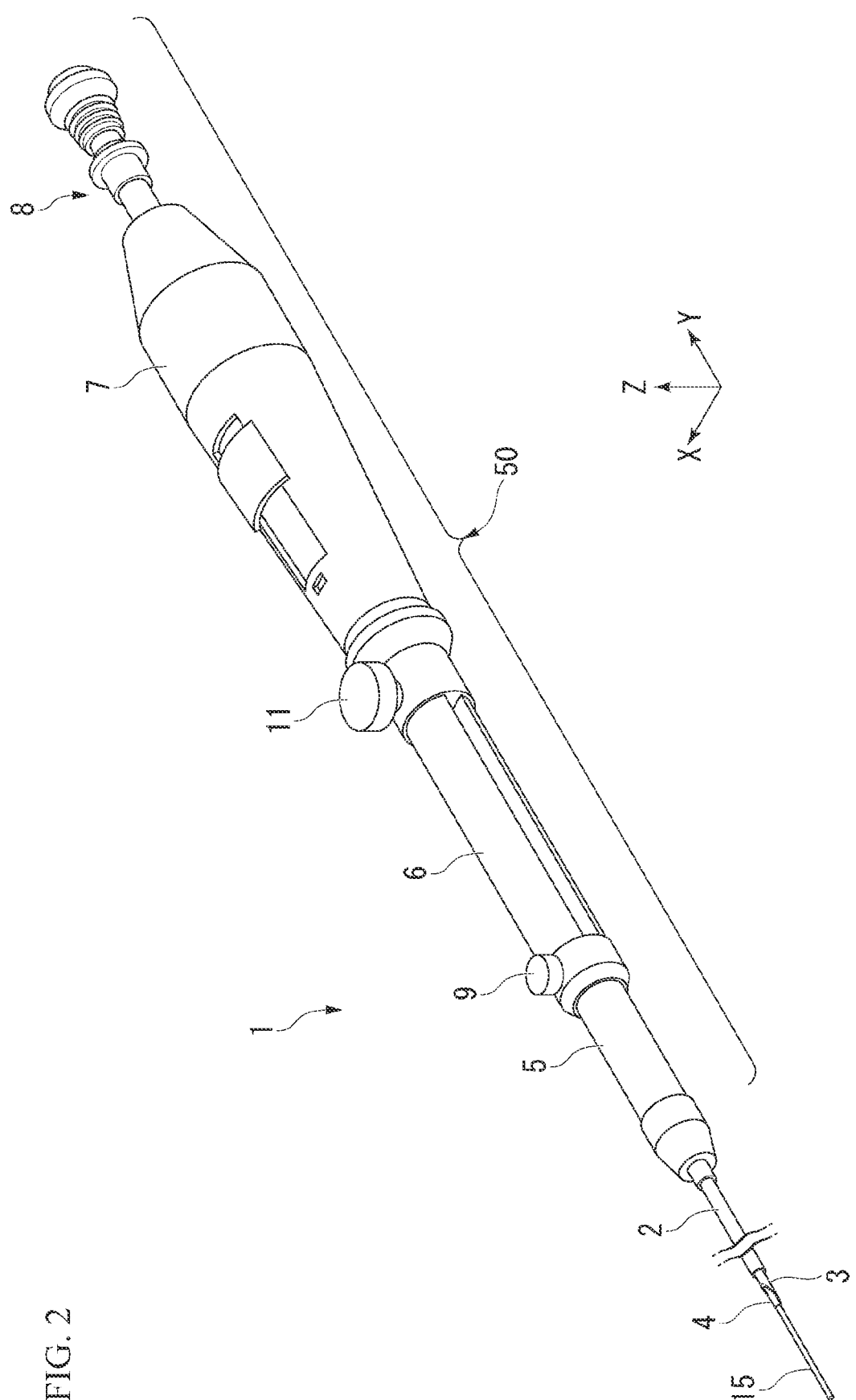
FIG. 2 is a perspective view showing an example of an overall configuration of the puncture device according to the first embodiment.

FIG. 2 is a perspective view showing the overall configuration of the puncture device according to the first embodiment.

As shown in FIG. 2, the puncture device 1 according to the present embodiment includes a tubular sheath 2 having a central axis O (longitudinal axis), a needle tube 3 movably disposed in the sheath 2 along the central axis O, a protective tube (inner tube) 4 movably disposed in the needle tube 3 in the central axis O direction, and an operation unit 50.

The puncture device 1 includes an operation unit 50 having an operation portion main body 5 grasped by a surgeon and an assistance thereof (hereinafter collectively referred to as a surgeon), a sheath slider 6 to which the proximal end of the sheath 2 is fixed and supported so as to be movable in the central axis O direction with respect to the operation portion main body 5, a needle slider 7 supported so as to be movable in the direction along the central axis O with respect to the sheath slider 6, and a tube slider 8 supported so as to be movable in the central axis O direction with respect to the needle slider 7.

Figure 3:
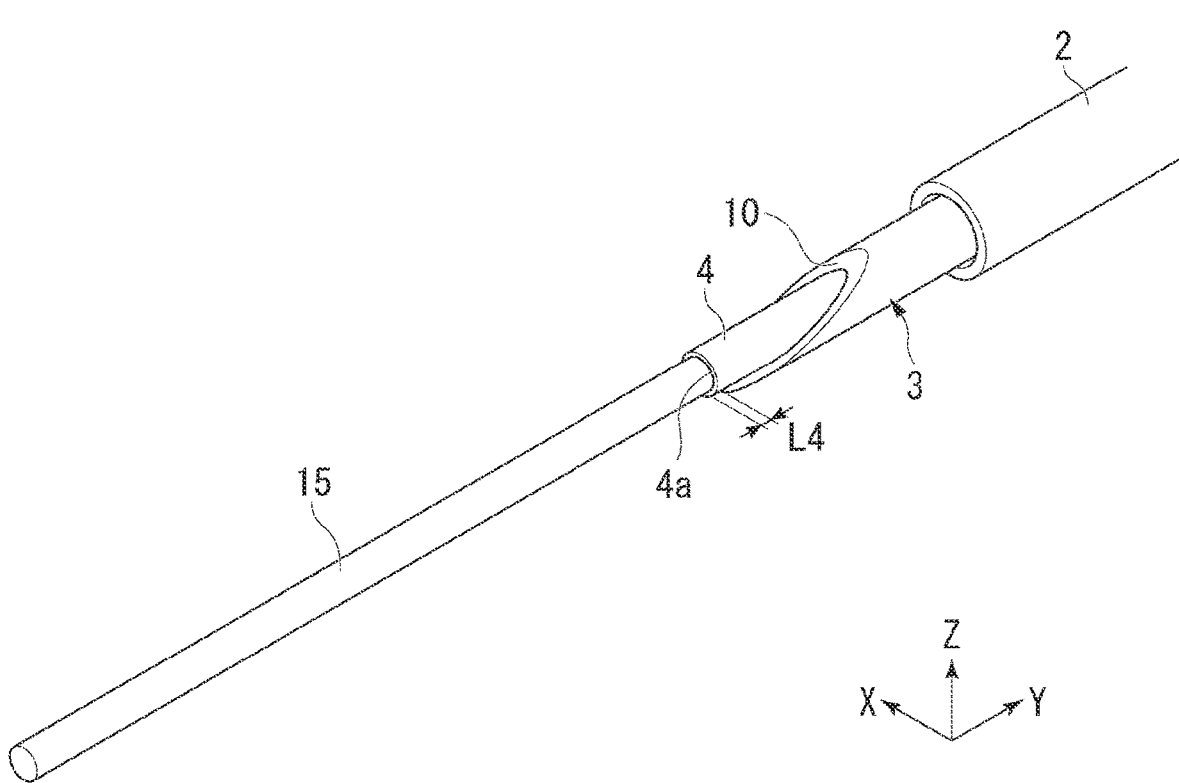
FIG. 3 is a perspective view showing an example of a configuration of the distal end side of the puncture device shown in FIG. 1.

FIG. 3 is a perspective view showing the configuration of the distal end side of the puncture device shown in FIG. 2.

As shown in FIG. 3, the sheath 2 is formed in a tubular shape having a circular cross section. The proximal end of the sheath 2 is fixed to the sheath slider 6.

As shown in FIG. 3 the needle tube 3 is formed in a cylindrical shape having an outer diameter slightly smaller than the inner diameter of the sheath 2. The needle tube 3 is inserted into the sheath 2 so as to be advanceable and retractable inside the sheath 2 in the central axis O direction. The needle tube 3 has a needle tip 10 having a shape such as by cutting obliquely with respect to the radial direction intersecting the central axis O at a distal end thereof. A proximal end of the needle tube 3 is fixed to a needle slider 7.

The protective tube 4, such as shown in FIG. 3, forms a slightly smaller cylindrical shape than the inner diameter of the needle tube 3. The protective tube 4 is inserted into the needle tube 3 so as to be advanceable and retractable in the central axis O direction. The inner diameter of the protective tube 4 is larger than the outer diameter of the guide wire 15. That is, the guide wire 15 may be inserted to be movable in the central axis O direction in the lumen (through hole) 4a included in the protective tube 4. The proximal end of the protective tube 4 is fixed to a tube slider 8. A contrast agent may be injected into the protective tube 4.

The protective tube 4 is made of a relatively rigid resin material such as the PEEK (polyether ether ketone resin) or the like. In addition, the polypropylene or the PET may be employed instead of the PEEK as the relatively rigid resin material. Also, the ABS, the PC, and other engineering plastic materials may be used as well as the reinforced plastic materials.

The protective tube 4 may be made of a material that can be detected by an ultrasonic sensor. Thus, it is possible to easily visually recognize the protrusion state of the protective tube 4 by the ultrasonic sensor.

Further, a metal powder or an X-ray contrast agent may be applied to the distal end portion of the protective tube 4. As a result, the protrusion state of the protective tube 4 can be easily visually recognized under X-rays or under an ultrasonic endoscope.

Figure 4:
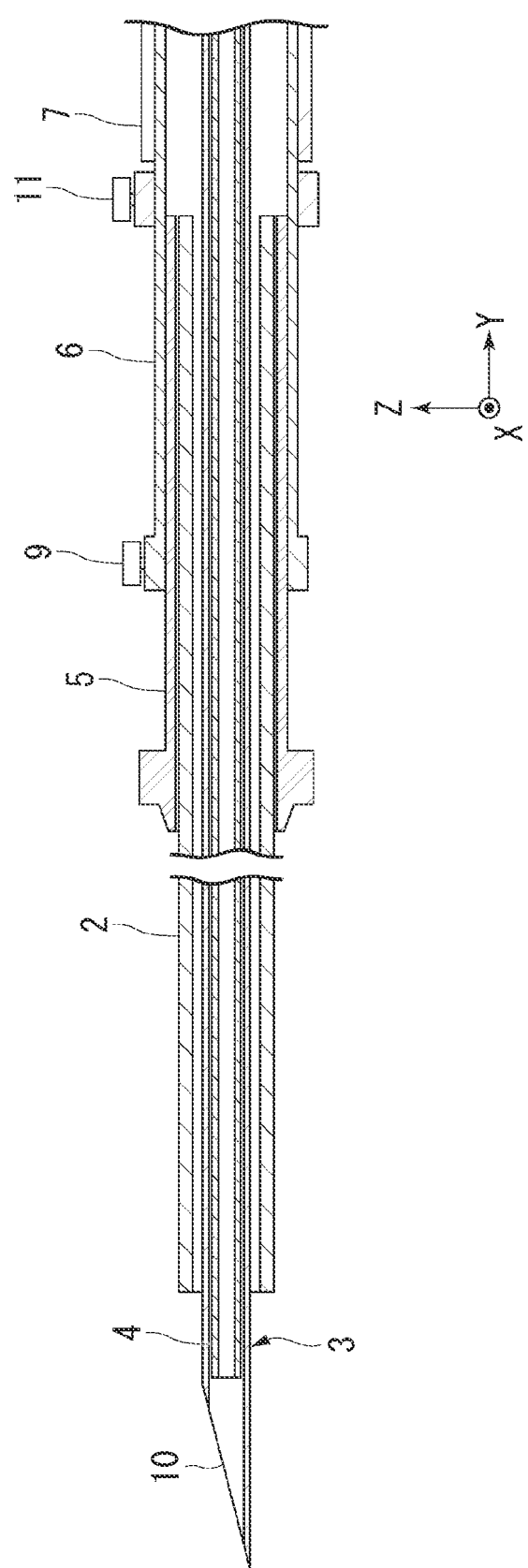
FIG. 4 is a partial cross-sectional view showing an example of a configuration of the puncture device in FIG. 1.

FIG. 4 is a partial cross-sectional view showing the configuration of the puncture device of FIG. 2.

The operation portion main body 5, as shown in FIG. 4 has an inner diameter larger than the outer diameter of the sheath 2. The sheath 2 is inserted into the operation portion main body 5 so as to advanceable and retractable in the central axis O direction.

As shown in FIG. 4, the sheath slider 6 has an inner diameter larger than the outer diameter of the sheath 2. The sheath 2 is disposed inside the sheath slider 6. The proximal end of the sheath 2 is fixed to the sheath slider 6. The sheath slider 6 is provided with a fixing member such as a threaded member such as a fixing screw 9 such as for fixing the sheath slider 6 at an arbitrary position with respect to the operation portion main body 5. When the fixing screw 9 is loosened, the sheath slider 6 is advanceable and retractable in the longitudinal direction with respect to the operation portion main body 5, and when the fixing screw 9 is tightened, the sheath slider 6 is not advanceable and retractable with respect to the operation portion main body 5. The sheath slider 6 is provided with a fixing member such as a threaded member such as a fixing screw or other needle stopper 11 configured to adjustably define the advanceable position of the needle slider 7 with respect to the sheath slider 6.

As shown in FIG. 4, the needle slider 7 has an inner diameter larger than the outer diameter of the needle tube 3. The needle tube 3 is disposed inside the needle slider 7 and the sheath slider 6. The proximal end of the needle tube 3 is fixed to the needle slider 7. It is possible to advance and retract the needle tube 3 in the central axis O direction with respect to the sheath 2 due to the movement of the needle slider 7 along the central axis O direction with respect to the sheath slider 6.

At this time, the advanceable position of the needle slider 7 is adjusted by the needle stopper 11 provided on the sheath slider 6. When the needle stopper 11 is loosened, the needle slider 7 is advanceable and retractable with respect to the sheath slider 6, and when the needle stopper 11 is tightened, the needle slider 7 is not advanceable and retractable with respect to the sheath slider 6.

Figure 5:
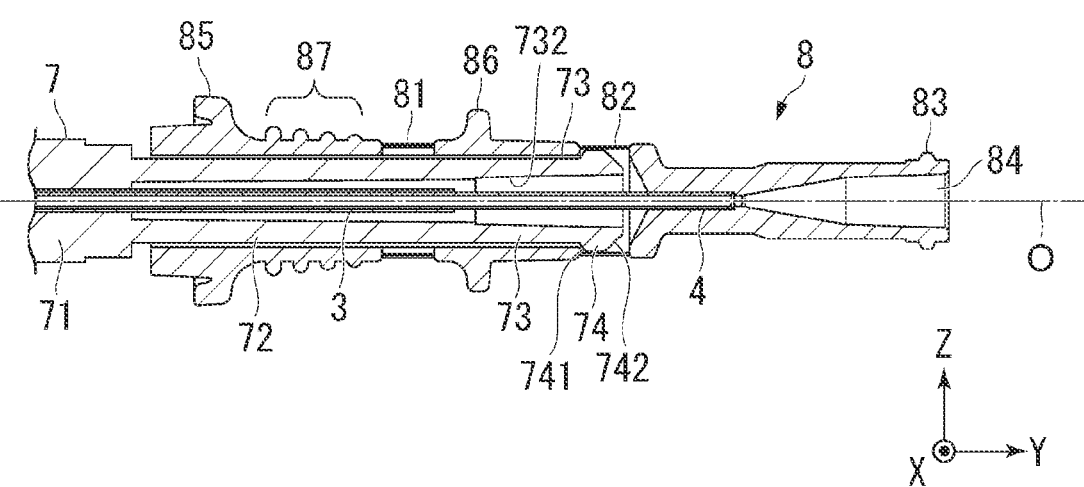
FIG. 5 is a partial cross-sectional view showing an example of a configuration of the puncture device shown in FIG. 1.

FIG. 5 is a partial cross-sectional view showing the configuration of the puncture device 1 shown in FIG. 2.

As shown in FIG. 5, the needle slider 7 includes a needle slider main body 71, a tube slider holder 72, an arm 73 provided at an end portion of the tube slider holder 72, and a stop or pawl or claw 74 provided at an end portion of the arm 73.

The tube slider holder 72 is provided at the proximal end of the needle slider 7 and has a cylindrical shape. As shown in FIG. 4 and FIG. 5, the needle tube 3 is disposed inside the tube slider holder 72. The tube slider holder 72 slidably supports the tube slider 8 such that the slider 8 is slidable along the longitudinal direction. That is, the tube slider 8 is advanceable and retractable in the longitudinal direction with respect to the tube slider holder 72. As shown in FIG. 5, the outer diameter of the tube slider holder 72 is smaller than the inner diameter of the tube slider 8.

The arm 73 is provided at the proximal end of the tube slider holder 72 and extends along the central axis O of the needle slider 7. The arm 73 is formed of an elastically deformable material, and it is possible to bend in the lateral or radial direction of the tube slider holder 72.

Figure 7:
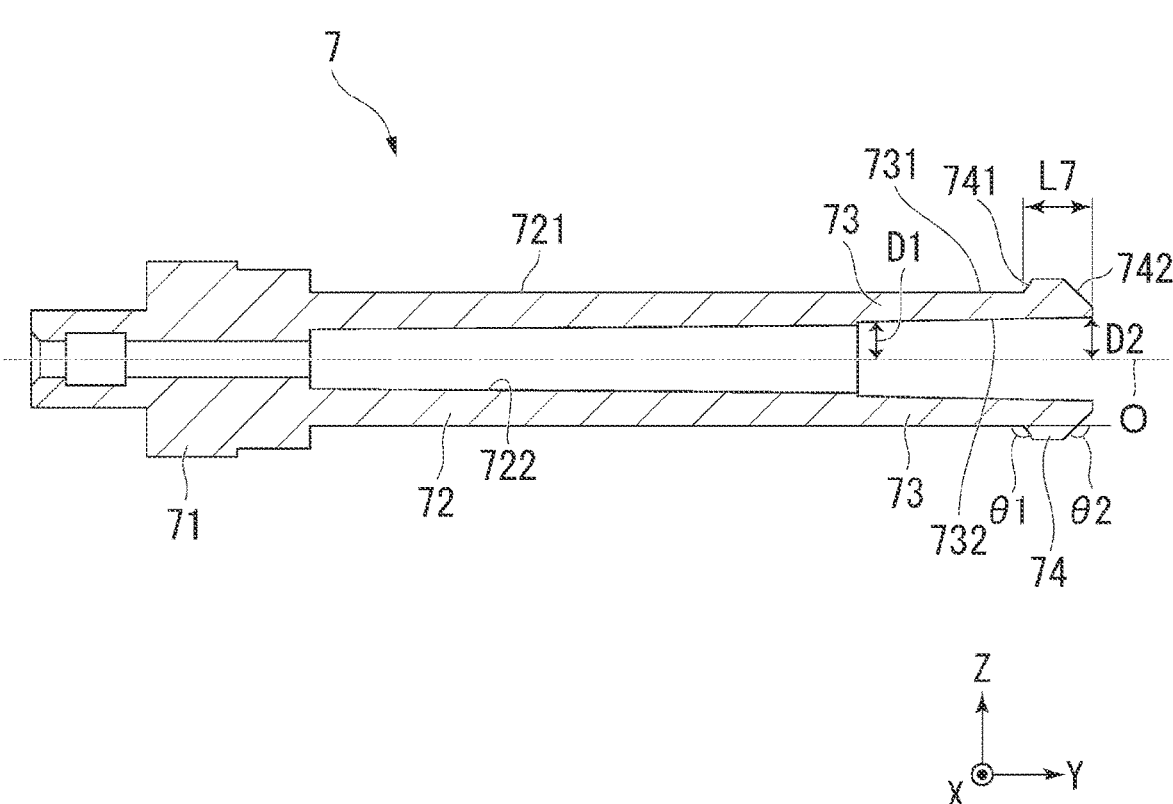
FIG. 7 is a cross-sectional view showing an example of a configuration of the needle slider 7.

As shown in FIG. 5 and FIG. 7, two of the arms 73 are provided to sandwich the central axis O of the needle slider 7, and the outer surface 731 of the arm 73 is positioned on an extension line of the outer peripheral surface 721 of the tube slider holder 72.

The inner surface 732 of the arm 73 is inclined in a direction separated from the central axis O of the needle slider 7 as it moves away from the tube slider holder 72. That is, with regard to a distance between the central axis O of the needle slider 7 and the inner surface 732 of the arm 73, a distance D2 at the proximal end side of the arm 73 (the direction where the injection port 84 is positioned) is larger than a distance D1 at the distal end side of the arm 73 (the direction where the needle tip 10 is positioned). Thus, the inner surface 732 of the arm 73 is inclined such that when the arm 73 is deformed so as to bend radially inwardly, the arm 73 is possible to prevent the interference between the arm 73 and the needle tube 3 and the protective tube 4 passing through the inside of the arm 73.

Additionally, an inclination angle of the inner surface 732 with respect to the central axis O of the needle slider 7 may not be fixed along the axial direction. As toward the proximal end side, the inclination angle with respect to the central axis O may be increased.

In the present embodiment, the inner surface 722 of the tube slider holder 72 may also be inclined in a direction separated from the central axis O of the needle slider 7 as from the needle slider main body 71 toward the arm 73. Thus, when the arm 73 is bent radially inwardly, it is possible to prevent the interference between the tube slider holder 72 and the needle tube 3 and the protective tube 4 passing through the inside of the tube slider holder 72.

Figure 6A:
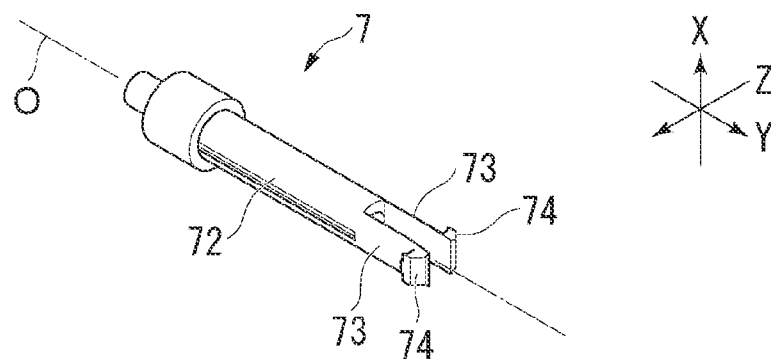
FIG. 6A is a perspective view showing an example of a configuration of the needle slider.
Figure 6B:
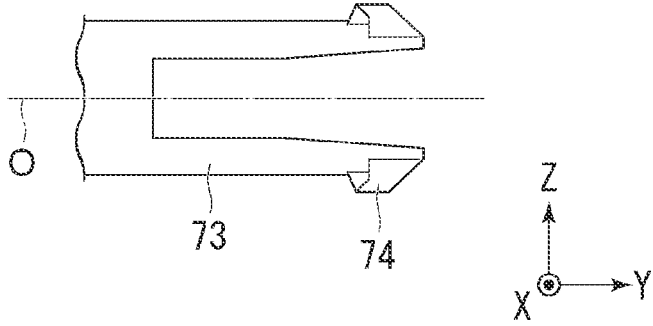
FIG. 6B is a side view showing an example of the configuration of a rear end of the needle slider as viewed from the X-direction.
Figure 6C:
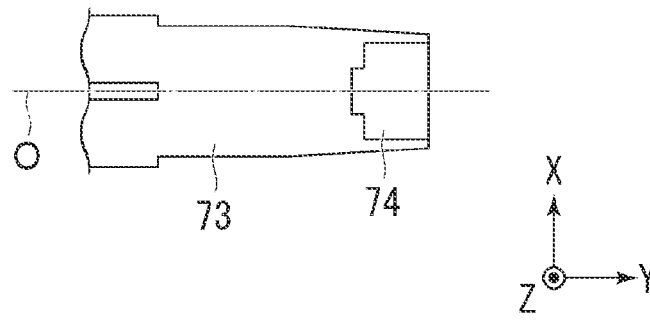
FIG. 6C is a side view showing an example of the configuration of the rear end of the needle slider as viewed from the Z-direction.

Referring to FIG. 6A to FIG. 6C and FIG. 7, the shape of the arm 73 of the needle slider 7 will be described. FIG. 6A is a perspective view showing a configuration of the needle slider 7. FIG. 6B is a side view showing the configuration of the proximal end of the needle slider 7 as viewed from the X-direction. FIG. 6C is a side view showing the configuration of the proximal end of the needle slider 7 as viewed from the Z-direction. FIG. 7 is a cross-sectional view showing the configuration of the needle slider 7.

As shown in FIG. 6A and FIG. 7, the arm 73 extends along the central axis O direction (Y direction) of the needle slider 7. At this time, a width in one direction (X direction) perpendicular to the Y direction is smaller than a width in the direction (Z direction) perpendicular to the X direction and the Y direction. A cross-sectional shape of the arm 73 in a plane (XZ plane) perpendicular to the central axis O of the needle slider 7 is, for example, a semicircle, an oval, a rectangle or the like, and the cross-sectional shape thereof is formed to have a thickness in the Z direction that is smaller than the width in the X direction. Accordingly, it is easy for the arm 73 to be easily elastically deformed in the thickness direction (Z direction) by receiving an external force. That is, the arm 73 may be bent in the radial direction of the tube slider holder 72.

As shown in FIG. 6A and FIG. 7, a length of the arm 73 in the longitudinal direction is longer than a length of the claw 74 in the longitudinal direction. In the present embodiment, for example, the claw 74 is provided in a quarter area on the proximal end side of the arm 73. Since the arm 73 has a predetermined length in the longitudinal direction, it is possible to displace the position of the claw 74 in the radial direction by a desired amount. By displacing the position of the claw 74 in the radial direction, as described later, it is possible to engage and disengage the claw 74 with respect to the locking portion 80.

In the above description, the aspect of providing two arms 73 are described, however, the number of the arms 73 is not limited thereto. As described below, it is only necessary that the claw provided in the arm 73 is engaged with the locking portion 80 (first locking portion 81 and second locking portion 82). Accordingly, the number of the arms 73 may be one or equal to three or more than three.

In the present embodiment, as shown in FIG. 6A, by providing two arms 73 to sandwich the central axis O of the needle slider 7 therebetween, it is possible to suppress the rattling of the arm 73 and the tube slider 8, and to reliably engage the claw 74 of the needle slider 7 with the first locking portion 81 or the second locking portion 82 of the tube slider 8. By providing the arm 73 at the claw 74, a force sensation is created when the claw 74 engages with the locking portion 80. Accordingly, it allows the surgeon or other user to perceive the engagement of the claw 74 and the locking portion 80.

The claw 74 is provided on the proximal end side of the arm 73 and extending radially outwardly. The claw 74 has inclined surfaces on the first surface 741 and the second surface 742, respectively. In the claw 74, the first surface 741 and the second surface 742 are inclined surfaces, respectively. The first surface 741 is inclined in a direction separated radially outwardly away from the central axis as toward the proximal end side. The second surface 742 is inclined in a direction radially inwardly toward the central axis as toward the proximal end side. The second surface 742 extends toward the central axis more than the first surface 741. That is, the claw 74 has a tapered shape to become thin at the distal end side thereof as it extends in a direction away from the central axis O of the needle slider 7.

More specifically, the first surface 741 is a surface facing the distal end side of the arm 73 (the direction in which the needle tip 10 is positioned). An angle $\theta 1$ between the outer surface 731 and the first surface 741 of the arm 73 is equal to or more than 90 degrees. The second surface 742 is a surface facing the proximal end side of the arm 73 (the direction in which the injection port 84 is positioned). An angle $\theta 2$ between the outer surface 731 and the second surface 742 of the arm 73 is equal to or more than 90 degrees.

Figure 8:
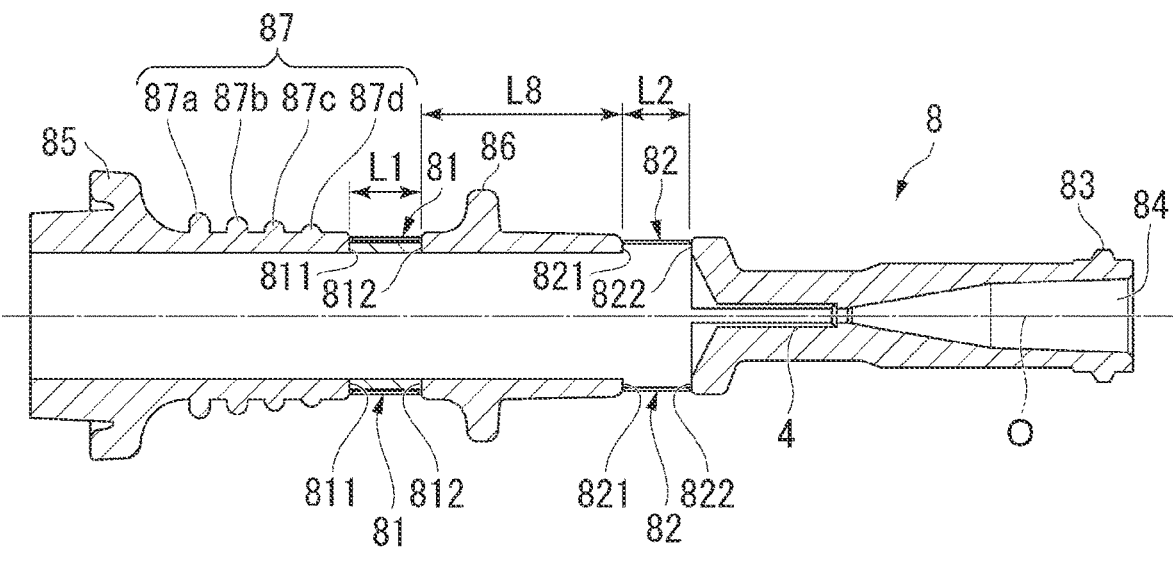
FIG. 8 is a cross-sectional view showing an example of a configuration of the tube slider.
Figure 8:
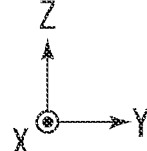

FIG. 8 is a cross-sectional view showing the configuration of the tube slider 8.

The tube slider 8 includes, as shown in FIG. 8, the first locking portion 81, the second locking portion 82, a mouthpiece 83 to which a syringe (injection device: see FIG. 9A) may be attached, an injection port 84 capable of introducing the contrast agent and a guide wire, a first large-diameter portion 85, a second large-diameter portion 86, and a step portion 87.

Inside the tube slider 8, the protective tube 4 is disposed as shown in FIG. 5. The proximal end of the protective tube 4 is fixed to the tube slider 8. By the tube slider 8 moving along the central axis O with respect to the needle slider 7, the protective tube 4 fixed to the tube slider 8 is advanceable and retractable along the central axis O with respect to the needle tube 3.

The first locking portion 81, as shown in FIG. 6A to FIG. 6C, is a concave portion in which the claw 74 provided in the tube slider 8 is engageable. The concave portion may penetrate the inner surface and the outer surface of the tube slider 8, or the concave portion may not penetrate the inner surface and the outer surface of the tube slider 8. More specifically, as shown in FIG. 5, the first locking portion 81 of the tube slider 8 includes a first surface 811 facing the first surface 741 of the claw 74 of the needle slider 7 and a second surface 812 facing the second surface 742 of the claw 74. As shown in FIG. 8, a length of the first locking portion 81 in the longitudinal direction of the tube slider 8, that is, the distance L1 between the first surface 811 and the second surface 812 is equal to or greater than a length L7 of the claw 74 in the longitudinal direction of the needle slider 7 shown in FIG. 7.

As shown in FIG. 5, the second locking portion 82 is a concave portion in which the claw 74 provided in the tube slider 8 is engageable. The concave portion may penetrate the inner surface and the outer surface of the tube slider 8, or the concave portion may not penetrate the inner surface and the outer surface of the tube slider 8. More specifically, as shown in FIG. 5, the second locking portion 82 of the tube slider 8 includes a first surface 821 (see FIG. 8) facing the first surface 741 of the claw 74 of the needle slider 7 and a second surface 822 (see FIG. 8) facing the second surface 742 (see FIG. 7) of the claw 74. As shown in FIG. 8, the length of the second locking portion 82 in the longitudinal direction, that is, the distance L2 between the first surface 821 and the second surface 822 is equal to or greater than the length L7 of the claw 74 (see FIG. 7) in the longitudinal direction.

As shown in FIG. 8, the second locking portion 82 of the tube slider 8 is provided on the proximal end side than the first locking portion 81 (the direction in which the injection port 84 is positioned). A Distance L8 between the first locking portion 81 and the second locking portion 82 in the longitudinal direction contributes to a protrusion length L4 (see FIG. 3) of the protective tube 4 to protrude from the distal end of the needle tube 3 as shown in FIG. 3. The protective tube 4 only has to be protruded from the needle tube 3 by a minimum length capable of protecting the guide wire 15 from the needle tip 10 of the needle tube 3. In the present embodiment, the protrusion length L4 of the protective tube 4 protruding from the needle tip 10 of the needle tube 3 is about 1 mm.

However, if a distance L8 between the first locking portion 81 and the second locking portion 82 in the longitudinal direction of the tube slider 8 is reduced to about 1 mm, the protective tube 4 does not protrude from the distal end of the needle tube 3 due to a change in the shape of the sheath 2 along the curved lumen, that is, a change in the path length of the protective tube 4.

Therefore, by defining the distance L8 between the first locking portion 81 and the second locking portion 82 in the longitudinal direction of the tube slider 8 to the desired distance, it is possible to protrude the protective tube 4 from the needle tube 3 by the minimum length capable of protecting the guide wire 15 from the needle tip 10. In the present embodiment, the distance L8 between the first locking portion 81 and the second locking portion 82 is about 20 mm. In such a structure, according to the present disclosure, L8 is equal to L4×A×total length of cylinder/1500 (mm). The parameter A is a constant between 1 and 100.

As shown in FIG. 8, the injection port 84 is provided on the proximal end side of the tube slider 8. The injection port 84 is an opening through which the contrast medium and the guide wire may be introduced. The injection port 84 communicates with the internal lumen of the protective tube 4.

As shown in FIG. 8, the first large-diameter portion 85 and the second large-diameter portion 86 are provided by partially protruding the outer peripheral surface of the tube slider 8 radially outwardly. The first large-diameter portion 85 and the second large-diameter portion 86 are formed to be disposed at intervals between each other in the longitudinal direction of the tube slider 8. In the present embodiment, the first large-diameter portion 85 and the second large-diameter portion 86 are formed at intervals slightly larger than the thickness of the finger of the surgeon. The outer diameter of the first large-diameter portion 85 is larger than the outer diameter of the second large-diameter portion 86, and the side surface of the first large-diameter portion 85 protrudes outwardly in the radial direction more than the side surface of the second large-diameter portion 86. In this manner, when the surgeon slides his/her finger along the outer surface of the tube slider 8, the finger will surely stop at the first large-diameter portion 85. Accordingly, even in a dark endoscope room or in a state in which the surgeon is watching at the endoscope screen without looking at operation portion 50, it is possible for the surgeon to securely grasp the first large-diameter portion 85.

The stepped portion 87 has a plurality of annular convex portions 87a to 87d having different dimensions in the radial direction from each other. In the present embodiment, four annular convex portions 87a to 87d are formed at substantially equal intervals in the longitudinal direction. The shape of the end face of each annular convex portion 87a to 87d at the outside in the radial direction is formed in a semicircular shape. The annular convex portions 87a to 87d are on the proximal end side of the first large-diameter portion 85 and formed between the first large-diameter portion 85 and the first locking portion 81. The annular convex portions 87a to 87d are arranged in this order from the distal end side, and the annular convex portion 87a positioned at the most distal end side has the largest outer diameter, and the outer diameters of the annular convex portions 87b to 87d are gradually decreased as toward the proximal end side.

Additionally, among the four annular convex portions 87a-87d, although the outer diameter of the annular convex portion 87a located at the most distal end side is the largest, the outer diameter of the annular convex portion 87a is smaller than the outer diameter of the first large-diameter portion 85 and the second large-diameter portion 86. Thus, by changing the outer diameter in steps, the surgeon can grasp the tube slider 8 securely even under non-visual conditions.

[Operations of Puncture Device 1]

The operations of the puncture device 1 according to the present embodiment will be described below.

Figure 9A:
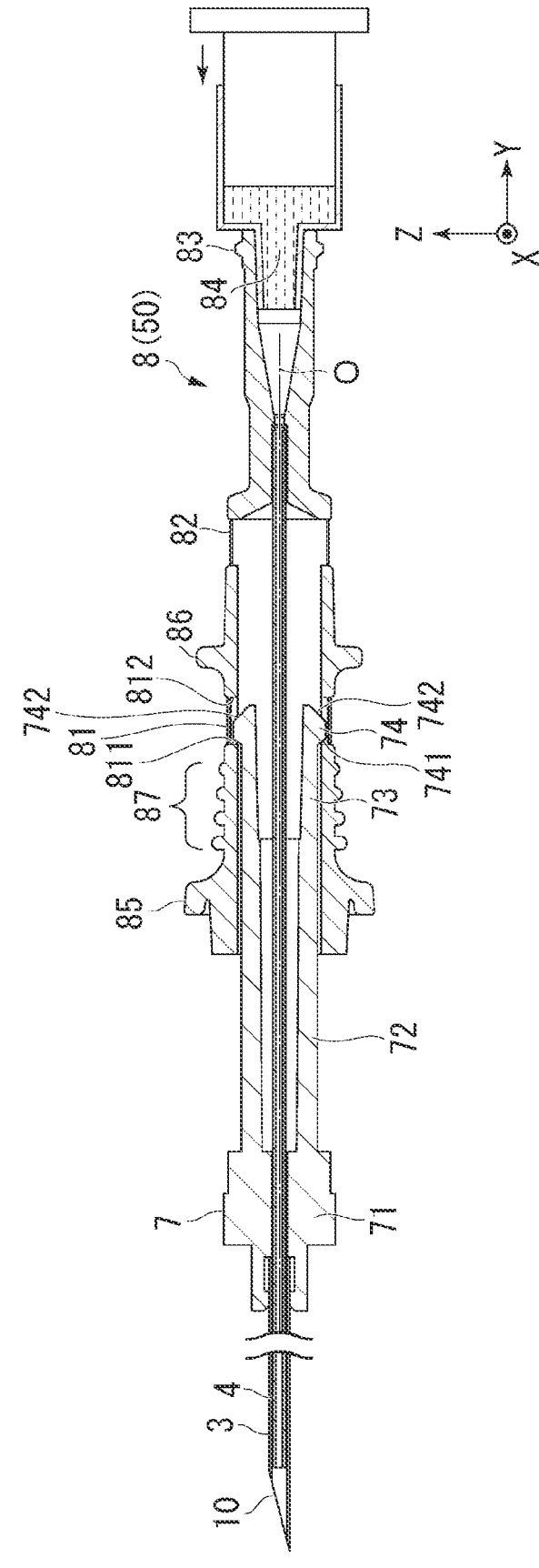
FIG. 9A is a view showing an example of an accommodation state in which a distal end of the protective tube is accommodated in the needle tube.
Figure 9B:
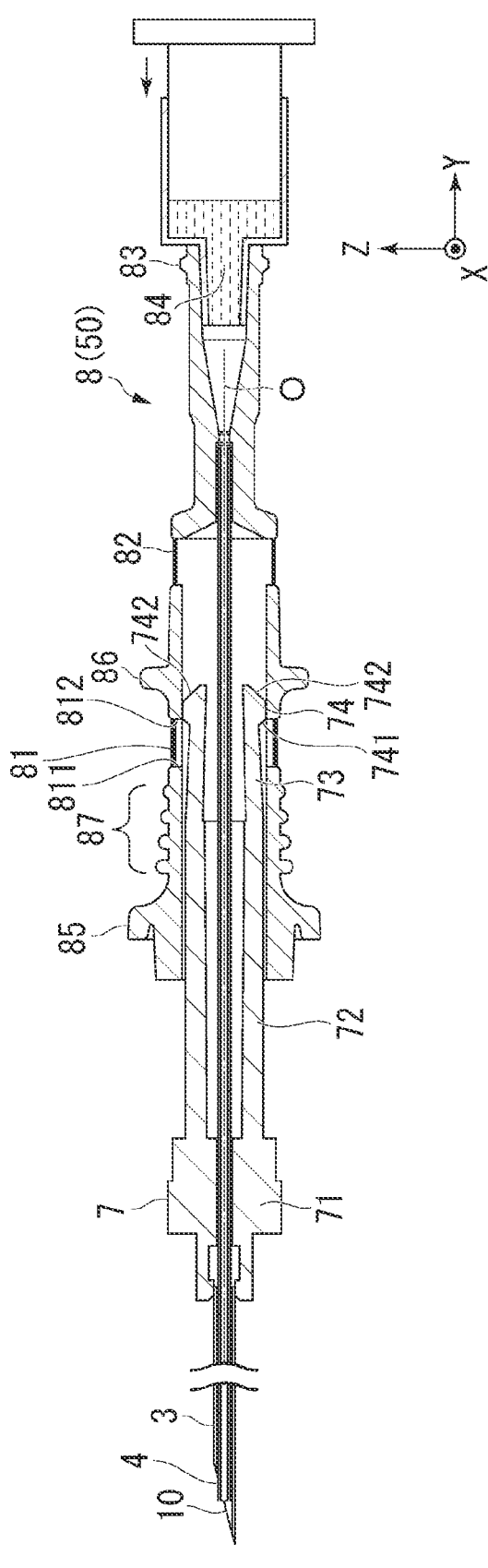
FIG. 9B is a view showing an example of a transition state in which the distal end of the protective tube has transitioned from the needle tube.

The puncture device 1 may take three states shown as below, that is, an accommodation state in which the distal end of the protective tube 4 is accommodated in the needle tube 3 (FIG. 9A), a protrusion state in which the distal end of the protective tube 4 is protruding at a maximum length from the needle tube 3 (FIG. 9C), and a transition state in the middle of transitioning from the accommodation state to the protrusion state (FIG. 9B). The sheath 2, the operation portion main body 5, and the sheath slider 6 are omitted in FIGS. 9A to 9C.

(Accommodation State)

FIG. 9A is a view showing the accommodation state in which the distal end of the protective tube 4 is located, positioned, or accommodated in the needle tube 3.

When the puncture device 1 is in the accommodation state, the distal end of the protective tube 4 is accommodated in the needle tube 3 as shown in FIG. 9A. At this time, the claw 74 of the needle slider 7 and the first locking portion 81 of the tube slider 8 are engaged with each other in the operation portion 50. Due to the engagement of the claw 74 with the first locking portion 81, the tube slider 8 cannot easily advance and retract in the longitudinal direction with respect to the needle slider 7. That is, in a state in which the distal end of the protective tube 4 is accommodated in the needle tube 3, the first locking portion 81 (locking portion 80) is configured to fix the longitudinal positions of the needle slider 7 and the tube slider 8.

Here, the accommodation state in which the distal end of the protective tube 4 is accommodated in the needle tube 3 refers to a state in which the entire protective tube 4 is accommodated in the needle tube 3, and the distal end of the protective tube 4 is located on the proximal side of the opening of the obliquely cut needle tip 10 and hidden in the needle tube 3.

(Protrusion State)

Figure 9C:
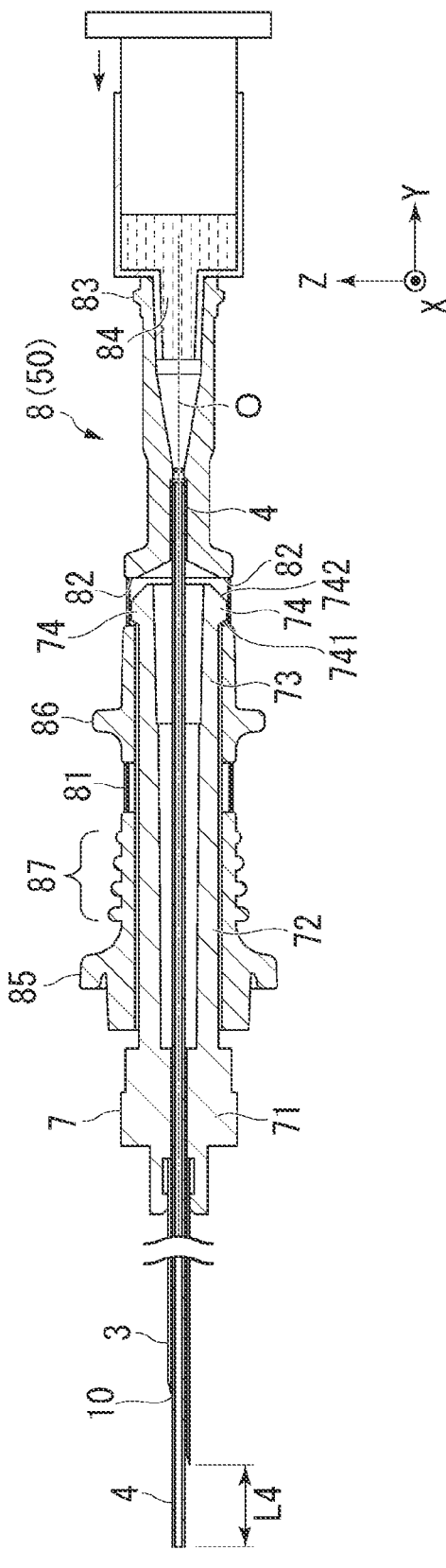
FIG. 9C is a view showing an example of a protrusion state in which the distal end of the protective tube protrudes from the needle tube.

FIG. 9C is a view showing a protrusion state in which the distal end of the protective tube 4 protrudes from the needle tube 3.

When the puncture device 1 is in the protrusion state, the distal end of the protective tube 4 protrudes the largest length from the distal end of the needle tip 10 of the needle tube 3 as shown in FIG. 9C. For example, in the present embodiment, the distal end of the protective tube 4 protrudes by about 1 mm from the distal end of the needle tip 10 of the needle tube 3. That is, the protrusion length L4 of the protective tube 4 shown in FIG. 9C is 1 mm.

Here, the appropriate design of the protrusion length L4 depends on the diameter of the organ (lumen) to be punctured. For example, if the puncture target is the intrahepatic bile duct and the diameter of the duct is 2-3 mm, such that the protrusion length L4 is equal to about 1 mm or less than 1 mm, and if the target is the common bile duct and the diameter is about 10 mm, such that the protrusion length L4 is equal to about 5 mm or less than 5 mm. For other organs, the protrusion length L4 should be equal to or less than half of the diameter (inner diameter) of the duct.

At this time, the claw 74 of the needle slider 7 and the second locking portion 82 of the tube slider 8 are engaged with each other in the operation portion 50. Due to the engagement of the claw 74 with the second locking portion 82, the tube slider 8 cannot easily advance and retract in the longitudinal direction with respect to the needle slider 7. That is, in the state in which the distal end of the protective tube 4 protrudes from the needle tube 3, the second locking portion 82 (locking portion 80) is configured to fix the longitudinal positions of the needle slider 7 and the tube slider 8.

(Transition State)

FIG. 9B is a view showing a transition state in which the distal end of the protective tube 4 has transitioned from the needle tube 3.

When the puncture device 1 is in the transition state, the distal end of the protective tube 4 protrudes slightly from the distal end of the needle tube 3 as shown in FIG. 9B. For example, the distal end of the needle tube 3 and the distal end of the protective tube 4 are located at substantially the same positions. At this time, in the operation portion 50, the arm 73 of the needle slider 7 is elastically deformed and bent inwardly in the radial direction to enter the inside of the tube slider 8. As a result, the engagement state of the claw 74 with respect to the first locking portion 81 or the second locking portion 82 is released, and the tube slider 8 is moveable in the longitudinal direction with respect to the needle slider 7. As the tube slider 8 moves in the longitudinal direction with respect to the needle slider 7, the claw 74 of the needle slider 7 is positioned between the first locking portion 81 and the second locking portion 82 while the arm 73 maintains the state of bending inwardly in the radial direction.

When the puncture device 1 is in the transition state, the claw 74 of the needle slider 7 is not engaged with the locking portion 80 of the tube slider 8 (first locking portion 81, the second locking portion 82). Accordingly, the tube slider 8 can easily advance and retract in the longitudinal direction with respect to the needle slider 7. A third locking portion (not shown) may be provided between the first locking portion 81 and the second locking portion 82 to ensure that the transition state is achieved.

The puncture device 1, by the tube slider 8 receiving an external force, is transitioned among the three states including the accommodation state (FIG. 9A), the protrusion state (FIG. 9C), and the transition state (FIG. 9B.

First, a situation in which the puncture device 1 is transitioned between the accommodation state and the transition state will be described below.

(Accommodation State to Transition State)

As shown in FIG. 9A, it is assumed that when the puncture device 1 is in the accommodation state, an external force having a first force amount is applied to the tube slider 8 from the proximal end toward the distal end in the longitudinal direction. At this time, since the claw 74 is engaged with the first locking portion 81, the tube slider 8 does not advance with respect to the needle slider 7. On the other hand, when the external force of a predetermined second force amount larger than the first force amount is applied to the tube slider 8, by the force is transmitted from the second surface 812 of the first locking portion 81 to the second surface 742 of the claw 74, the elastic deformation is occurred in the arm 73. The arm 73 is elastically deformed to be bent inwardly in the radial direction such that the engagement between the claw 74 and the first locking portion 81 is released, and the puncture device 1 is transitioned from the accommodation state (FIG. 9A) to the transition state (FIG. 9B).

At this time, since the second surface 742 of the claw 74 described above is the inclined surface, it is possible to elastically deform the arm 73 inwardly in the radial direction by a smaller second force amount. That is, the engagement between the claw 74 and the first locking portion 81 may be released with a smaller second force amount.

(Transition State to Accommodation State)

On the other hand, as shown in FIG. 9B, when the puncture device 1 is in the transition state, if the external force is applied to the tube slider 8 from the distal end toward the proximal end in the longitudinal direction, the tube slider 8 retracts with respect to the needle slider 7. That is, in the longitudinal direction, when the claw 74 of the needle slider 7 is moved to the same position as the first locking portion 81 of the tube slider 8, the elastic deformation of the arm 73 which has maintained the state of being elastically deformed by the tube slider 8 is released. Then, the claw 74 engages with the first locking portion 81. In this manner, the puncture device 1 is transitioned from the transition state (FIG. 9B) to the accommodation state (FIG. 9A).

Next, a situation in which the puncture device 1 is transitioned between the transition state and the protrusion state will be described.

(Protrusion State to Transition State)

When the puncture device 1 is in the protrusion state (FIG. 9C), it is assumed that an external force having the first force amount is applied to the tube slider 8 from the distal end toward the proximal end in the longitudinal direction. At this time, the claw 74 of the needle slider 7 engages with the second locking portion 82 of the tube slider 8 such that the tube slider 8 does not retreat with respect to the needle slider 7. On the other hand, when the external force having a predetermined second force amount larger than the first force amount is applied to the tube slider 8, the force is transmitted from the first surface 821 of the second locking portion 82 to the first surface 741 of the claw 74 such that the elastic deformation is occurred in the arm 73. By the arm 73 being elastically deformed to be bent inwardly in the radial direction, the engagement between the claw 74 and the second locking portion 82 is released and the puncture device 1 is transitioned from the protrusion state (FIG. 9C) to the transition state (FIG. 9B).

At this time, since the first surface 741 of the claw 74 as described above is the inclined surface, it is possible to elastically deform the arm 73 with a smaller second force amount. That is, the engagement between the claw 74 and the second locking portion 82 may be released with a smaller second force amount.

(Transition State to Protrusion State)

On the other hand, when the puncture device 1 is in the transition state (FIG. 9B), if an external force is applied to the tube slider 8 from the proximal end toward the distal end in the longitudinal direction, the tube slider 8 advances with respect to the needle slider 7. When the claw 74 is moved to the same position as the second locking portion 82 in the longitudinal direction, the elastic deformation of the arm 73 which has maintained the state of being elastically deformed is released by the tube slider 8. Then, the claw 74 and the second locking portion 82 is engaged. In this manner, the puncture device 1 is transitioned from the transition state (FIG. 9B) to the protrusion state (FIG. 9C).

[Usage Method of Puncture Device 1]

A usage method of the puncture device 1 according to the present embodiment will be described below with reference to FIG. 10.

Figure 10:
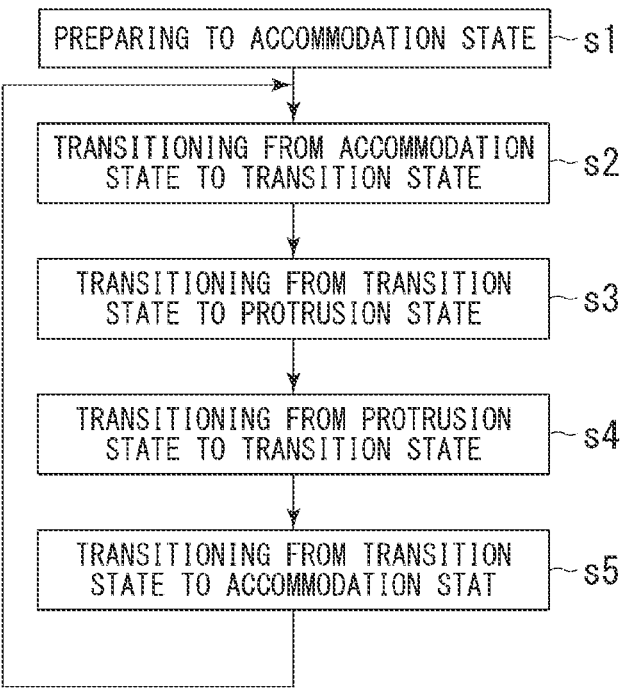
FIG. 10 is a flowchart showing an example of a usage method of a puncture device according to the embodiment.

FIG. 10 is a flowchart showing a usage method of a puncture device according to the present embodiment.

First, as shown in FIG. 10, the puncture device 1 is prepared to enter the accommodation state (FIG. 9A) (Step s1).

In Step s1, the puncture device 1 is prepared to enter the accommodation state (FIG. 9A). The surgeon adjusts the positions of the tube slider 8 and the needle slider 7 in the longitudinal direction such that the claw 74 of the needle slider 7 is locked to the first locking portion 81 provided on the tube slider 8. Thus, the puncture device 1 is transitioned into the accommodation state.

Next, the puncture device 1 is transitioned to the transition state (FIG. 9B) (Step s2).

In Step s2, the puncture device 1 is transitioned from the accommodation state to the transition state. When the puncture device 1 is in the accommodation state, the relative movement of the needle slider 7 and the tube slider 8 is restricted by the claw 74 and the first locking portion 81. The surgeon moves the tube slider 8 from the proximal end side to the distal end side with respect to the needle slider 7. At this time, the tube slider 8 is moved by a force amount larger than the locking force of the first locking portion 81 and the claw 74. Then, the arm 73 is deformed and the locking of the first locking portion 81 and the claw 74 is released. As a result, the puncture device 1 enters the transition state.

Subsequently, the puncture device 1 is transitioned to the protrusion state (FIG. 9C) (Step s3).

In Step s3, the puncture device 1 is transitioned from the transition state to the protrusion state. The surgeon moves the tube slider 8 from the proximal end side to the distal end side with respect to the needle slider 7. At this time, the tube slider 8 is further moved to the distal end side than the step s2. Then, the second locking portion 82 and the claw 74 are engaged with each other. As a result, the puncture device 1 enters the protrusion state.

Next, the puncture device 1 is transitioned from the protrusion state to the transitioned state (Step s4).

In Step s4, the puncture device 1 is transitioned from the protrusion state to the transition state. When the puncture device 1 is in the protrusion state, the relative movement of the needle slider 7 and the tube slider 8 is restricted by the claw 74 and the second locking portion 82. The surgeon moves the tube slider 8 from the distal end side to the proximal end side with respect to the needle slider 7. At this time, the tube slider 8 is moved by a force amount larger than the locking force of the second locking portion 82 and the claw 74. Then, the arm 73 is deformed and the engagement of the second locking portion 82 and the claw 74 is released. As a result, the puncture device 1 enters the transition state.

Next, the puncture device 1 is transitioned from the transition state to the accommodation state (Step s5).

In Step s5, the puncture device 1 is transitioned from the transition state to the accommodation state. The surgeon moves the tube slider 8 from the distal end side to the proximal end side with respect to the needle slider 7. At this time, the tube slider 8 is further moved to the proximal end side than in step s4. Then, the first locking portion 81 and the claw 74 are engaged with each other. Accordingly, the puncture device 1 enters the accommodation state.

The sequence of each step is not limited thereto.

For example, after performing the transition from the protrusion state to the transition state (Step s4), the operations may be performed in a sequence of transitioning the state from the transition state to the protrusion state (Step s3). Further, after performing the transition from the accommodation state to the transition state (Step s2), the operations may be performed in a sequence of transitioning the state from the transition state to the accommodation state (Step s5). Alternatively, after performing the transition from the transition state to the accommodation state (Step s5), the operations may be performed in a sequence of transitioning the state from the accommodation state to the transition state (Step s2).

[Usage Method of Guide Wire 15 by Using Puncture Device 1]

Figure 11:
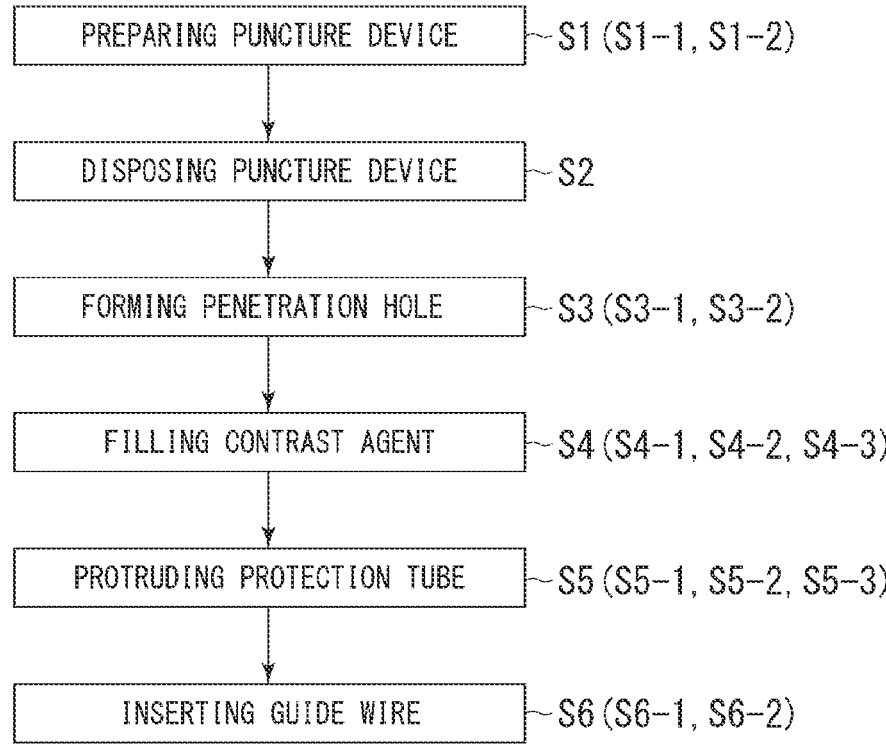
FIG. 11 is a flowchart showing an example of the operation steps of the puncture device according to the first embodiment.

A usage method of the guide wire 15 by using the puncture device 1 according to the present embodiment will be described below with reference to FIG. 11. FIG. 11 is a flowchart showing operation steps of the puncture device 1 according to the first embodiment.

First, the puncture device 1 is prepared to be in a usable state (Step S1).

In Step S1, the puncture device 1 is prepared to be ready for use.

First, by retracting the needle slider 7 to the most proximal end with respect to the sheath slider 6 (Step S1-1), the needle tip 10 of the needle tube 3 is disposed in a position to be accommodated in the sheath 2. Further, the tube slider 8 is retracted to the most proximal end with respect to the needle slider 7 (Step S1-2). As a result, the distal end of the protective tube 4 is arranged on the proximal side of the needle tip 10 of the needle tube 3. By these steps such as Step S1-1 and Step S1-2, the preparation of the puncture device 1 is completed.

The order of Step S1-1 and Step S1-2 may be reversed.

Next, the puncture device 1 is disposed at a desired position in the body cavity (Step S2).

In Step S2, the puncture device 1 is disposed at a desired location in the body cavity.

The sheath 2 of the prepared puncture device 1 is inserted from the proximal end opening of the channel 107 of the ultrasonic endoscope (endoscope) 100 including the ultrasonic sensor (not shown) to the vicinity of the distal end position of the channel 107. In this state, the ultrasonic sensor is operated to acquire a tomographic image in the body, and the ultrasonic endoscope 100 is inserted into a first lumen such as the stomach or the duodenum while confirming the acquired tomographic image. Then, the distal end opening of the channel 107 provided in the ultrasonic endoscope 100 is disposed to face the site to be pierced of the lumen wall of the first lumen.

Subsequently, a through-hole is formed in the lumen (Step S3)

In step S3, a through hole is formed in the lumen.

First, the sheath slider 6 is advanced with respect to the operating portion main body 5 in a state in which the distal end opening of the channel 107 is disposed to face the site to be pierced (Step S3-1). Accordingly, the distal end of the sheath 2 is protruded from the distal end opening of the channel 107.

Then, the needle slider 7 is advanced relative to the sheath slider 6 with the distal end of the sheath 2 disposed to face the site to be pierced of the lumen wall of the first lumen (Step S3-2). Thus, the needle tip 10 of the needle tube 3 is protruded from the inside of the sheath 2, and the needle tube 3 is punctured into the lumen wall of the first lumen being opposite to the distal end of the sheath 2. By puncturing the needle tube 3 into the lumen wall of the first lumen, the needle tube 3 is also punctured into a second lumen such as a bile duct or a pancreatic duct adjacent to the first lumen, thereby forming the through hole. At the time of forming the through hole, the distal end of the needle tube 3 is disposed inside the second lumen. The puncture device 1 is in the accommodation state in which the distal end of the protective tube 4 is accommodated in the needle tube 3

Next, a contrast agent is injected into the lumen (Step S4)

In step S4, a contrast agent is injected into the second lumen in the accommodation state in which the distal end of the protective tube 4 is accommodated in the needle tube 3. In the accommodation state, since the claw 74 of the needle slider 7 is engaged with the first locking portion 81 of the tube slider 8, the positions of the needle tube 3 and the protective tube 4 are fixed. In this state, a syringe filled with the contrast agent is attached to the mouthpiece 83 of the tube slider 8 (Step S4-1). When the syringe is attached thereto, an inner cylinder of the syringe is pushed forward while an outer cylinder of the syringe is pressed (Step S4-2). That is, when the inner cylinder of the syringe is pushed forward, the surgeon restricts the movement of the outer cylinder of the syringe in the longitudinal direction. By Step S4-2, the contrast agent flows through the injection port 84 into the protective tube 4.

At this time, the force amount for pushing the inner cylinder of the syringe out is increased based on the viscosity of the contrast agent and the inner diameter of the protective tube 4 through which the contrast agent is inserted. If the force amount for pushing the inner cylinder of the syringe increases, it is possible that the surgeon is not able to restrict the movement of the outer cylinder of the syringe in the longitudinal direction. When the puncture device 1 is in the accommodation state, by the first locking portion 81 (locking portion 80), the movement of the tube slider 8 with respect to the needle slider 7 is restricted. Therefore, even when the surgeon cannot restrict the movement of the outer cylinder of the syringe in the longitudinal direction, the unintentional advancement of the tube slider 8, that is, the advancement of the protective tube 4 can be prevented.

Once the injection of contrast agent is completed, the syringe is removed from the tube slider 8 (Step S4-3). At the time of preparing the puncture device 1 (Step S1), the syringe containing the contrast agent may be attached to the mouthpiece 83 of the puncture device 1.

Subsequently, the protective tube 4 is protruded from the needle tube 3 (Step S5).

In Step S5, after the fixation of the positions of the needle tube 3 and the protective tube 4 is released, the protective tube 4 is protruded from the needle tube 3. The tube slider 8 is advanced with respect to the needle slider 7 in the state in which the needle tube 3 is protruded to a position penetrating the through hole (Step S5-1). When the tube slider 8 is advanced, the protective tube 4 is advanced with respect to the needle tube 3 to a position where the distal end of the protective tube 4 protrudes from the needle tip 10 of the needle tube 3. At this time, by advancing the tube slider 8 by applying a predetermined force amount to the tube slider 8, the engagement between the claw 74 and the first locking portion 81 is released and the protective tube 4 is advanced. At this time, the puncture device 1 is transitioned from the accommodation state to the transition state.

In Step S5-2, the tube slider 8 is further advanced with respect to the needle slider 7 from the Step S5-1. Thus, the claw 74 and the second locking portion 82 are engaged with each other. At this time, the puncture device 1 is transitioned from the transition state to the protrusion state.

Additionally, there is no necessary to perform Step S5-1 and Step S5-2 intermittently, and these steps may be seamlessly performed.

At this time, the puncture device 1 in the protrusion state may be transitioned to the transition state and the accommodation state again. In this case, the tube slider 8 is retracted with respect to the needle slider 7 (Step S5-3). As the tube slider 8 moves, the claw 74 and the locking portion 80 are engaged with each other or disengaged from each other.

Finally, the guide wire 15 is inserted into the second lumen (Step S6).

In step S6, a guidewire 15 is inserted into the second lumen. In the state in which the protective tube 4 is protruded from the needle tube 3, the guidewire 15 is inserted into the lumen of the protective tube 4 through the injection port 84 (Step S6-1). The distal end of the guidewire 15 is disposed inside the second lumen. By protruding the guide wire 15 from the distal end of the protective tube 4, it is possible to prevent the guide wire 15 from coming into contact with the needle tip 10. That is, since the protective tube 4 is disposed in a state of being disposed on the inner surface of the needle tip 10, it is possible to reliably prevent the guide wire 15 that is protruded from and retracted into the distal end of the protective tube 4 from coming into contact with the needle tip 10 to be scrapped.

Subsequently, the needle tube 3 and the protective tube 4 are removed from the through-hole (Step S6-2). Accordingly, the guidewire 15 is indwelled in an extended state from the first lumen to the second lumen.

After the guidewire 15 is indwelled in the first lumen and the second lumen by Step S6, the procedure can proceed as appropriate. For example, in a case of indwelling a stent, a distal end portion of a stent supply device (not shown) is inserted into the bile duct along the guide wire 15 disposed in the bile duct from the stomach. After the stent is supplied from the stent supply device with the distal end thereof inserted into the bile duct, and the distal end of the supplied stent is expanded in the bile duct (second lumen), the proximal end of the stent is expanded in the stomach (first lumen) such that the lumen wall of the stomach and the lumen wall of the bile duct can be joined by the stent.

Also, before the stent is delivered to the position on the lumen wall of the bile duct, a device such as a balloon dilator for dilating the hole on the lumen wall may be inserted along the guidewire 15 to the vicinity of the lumen wall of the bile duct to expand the hole on the lumen wall of the bile duct in advance prior to indwelling the stent. The extension of the hole on the lumen wall is not limited to the lumen wall of the bile duct, but may be performed only on the lumen wall of the stomach or on both of the lumen wall of the bile duct and the lumen wall of the stomach.

Modification Example 1

Figure 12:
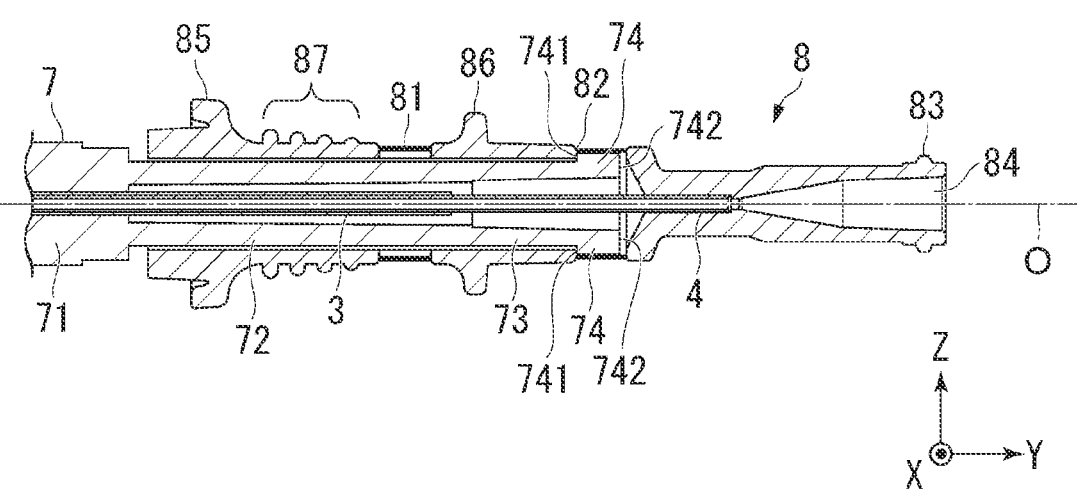
FIG. 12 is a view showing an example of a configuration according to a first modification example of the first embodiment.

FIG. 12 is a view showing a configuration of a first modification example of the first embodiment.

A first modification example of the puncture device 1 will be described with reference to FIG. 12. In the following description, the same configurations as those already described will be designated with the same reference signs and the duplicate descriptions will be omitted.

In the first modification example, the first surface 741 and the second surface 742 of the claw 74 do not have the inclined surfaces. That is, as shown in FIG. 12, the claw 74 has a shape along the concave portion of the first locking portion 81 and the second locking portion 82. More specifically, the first surface 741 of the claw 74, the first surface 811 of the first locking portion 81, and the first surface 821 of the second locking portion 82 extend substantially parallel toward the radial direction. Further, the second surface 742 of the claw 74, the second surface 812 of the first locking portion 81 and the second surface 822 of the second locking portion 82 extend substantially parallel toward the radial direction. Here, as described before, the first locking portion 81 and the second locking portion 82 are openings penetrating in the direction perpendicular to the central axis O.

The surgeon may push the claw 74 from the openings of the first locking portion 81 and the second locking portion 82 to deform the arm 73 inwardly in the radial direction. Similar to the first embodiment, by the arm 73 being elastically deformed, it is possible to release the engagement between the claw 74 and the locking portion 80. In order to make it easier for the surgeon to press the claw 74, the claw 74 may have an area large enough to be pressed directly with a finger, or the claw 74 may protrude radially outwardly than the second locking portion 82.

Without providing the inclined surfaces on the first surface 741 and the second surface 742 of the claw 74, the relative movement between the tube slider 802 and the needle slider 702 may be regulated more reliably than that in the first embodiment.

Second Embodiment

Next, a second embodiment of the puncture device 1 will be described with reference to FIG. 13 and FIG. 14A to FIG. 14C. In the following description, the same configurations as those already described are designated with the same reference numerals, and duplicate descriptions are omitted. The sheath 2, the operation portion main body 5, and the sheath slider 6 are omitted in FIG. 13 and FIG. 14A to FIG. 14C.

Figure 13:
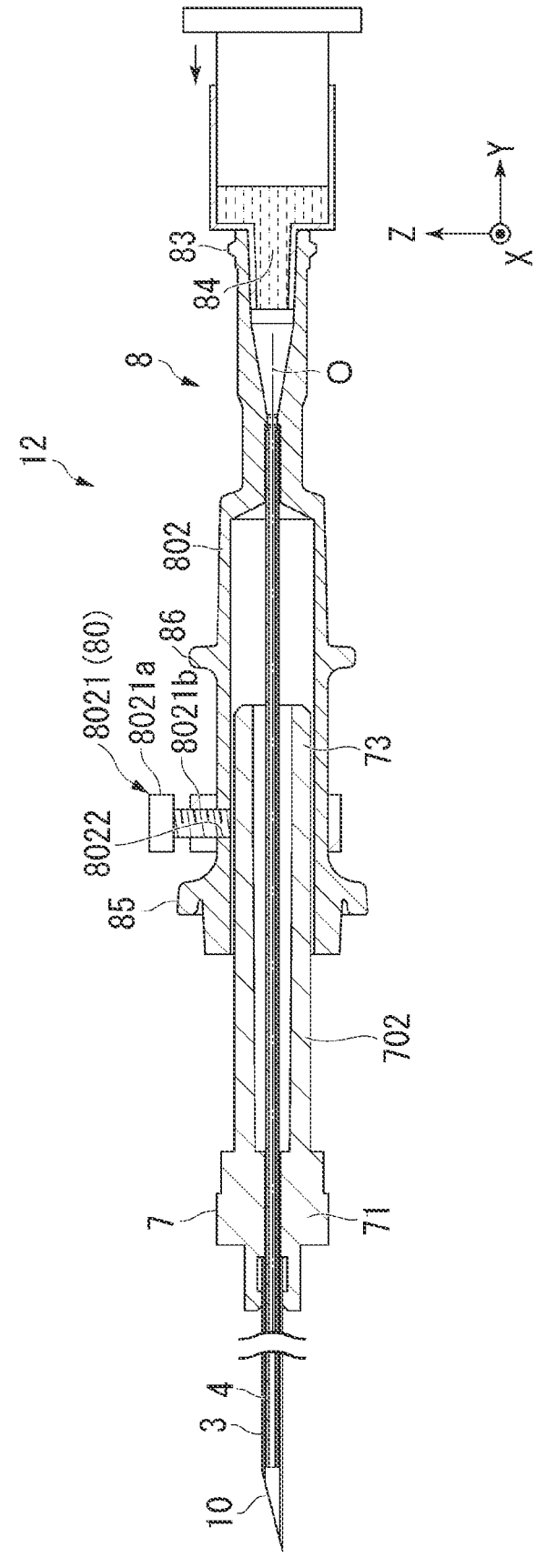
FIG. 13 is a cross-sectional view showing an example of a schematic configuration of the puncture device according to a second embodiment.
Figure 14A:
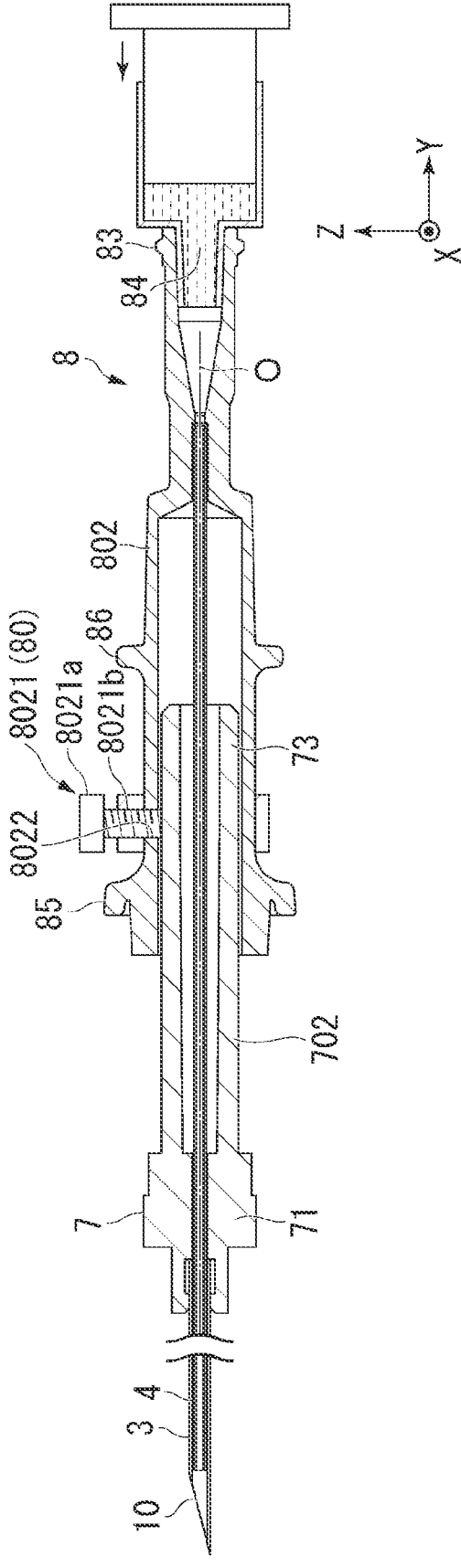
FIG. 14A is an example of a cross-sectional view showing an accommodation state in which the distal end of the protective tube is accommodated in the needle tube.
Figure 14B:
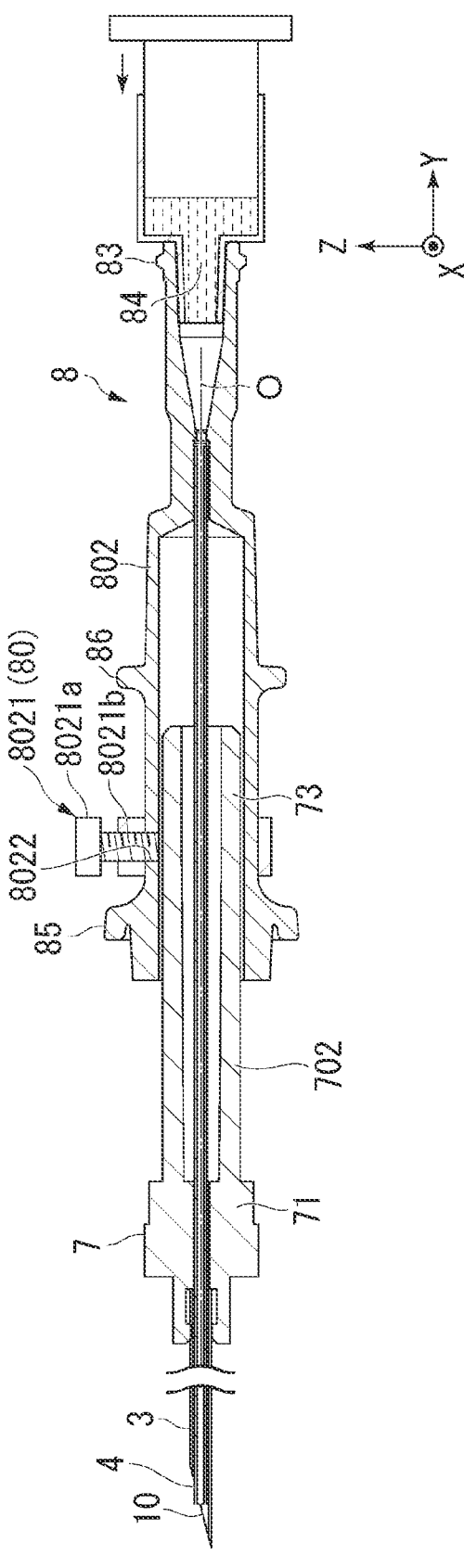
FIG. 14B is an example of a cross-sectional view showing a puncturing state in which the distal end of the protective tube is punctured from the needle tube.
Figure 14C:
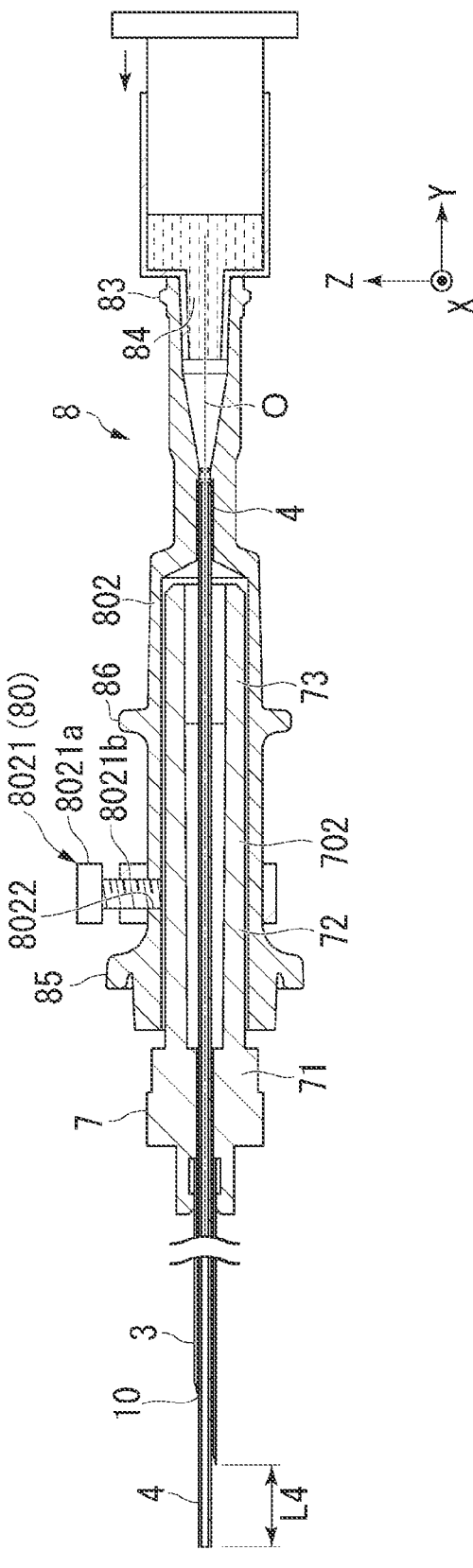
FIG. 14C is an example of a cross-sectional view showing a protrusion state in which the distal end of the protective tube protrudes from the needle tube.

FIG. 13 is a cross-sectional view showing a schematic configuration of the puncture device according to the second embodiment. FIG. 14A is a cross-sectional view showing an accommodation state in which the distal end of the protective tube 4 is accommodated in the needle tube 3. FIG. 14B is a cross-sectional view showing a puncturing state in which the distal end of the protective tube 4 is punctured from the needle tube 3. FIG. 14C is a cross-sectional view showing a protrusion state in which the distal end of the protective tube 4 protrudes from the needle tube 3.

As shown in FIG. 13, the puncture device 12 according to the second embodiment is different from the first embodiment in the configurations of the needle slider 702 and the tube slider 802. The needle slider 702 according to the present embodiment as shown in FIG. 13 does not include the arm 73 and the claw 74 as described in the first embodiment. The tube slider 802 does not include the first locking portion 81 and the second locking portion 82 as described in the first embodiment, and a screw (locking portion) 8021 and a nut hole 8022 are included instead.

As shown in FIG. 13, the movement of the tube slider 802 with respect to the needle slider 702 in the longitudinal direction according to the present embodiment is restricted by a screw 8021.

The screw 8021 includes a head portion 8021a having a substantially cylindrical shape and a shaft portion 8021b. The head portion 8021a has a cylindrical shape. The head portion 8021a is a portion operated by the surgeon, and the head portion 8021a has a size suitable for the surgeon to operate. The shaft portion 8021b has a threaded groove that can be screwed into the nut hole 8022 formed in the tube slider 802. The nut hole 8022 is a hole penetrating the circumferential wall of the tube slider 802 in a direction perpendicular to the longitudinal direction. The screw 8021 can be screwed into the nut hole 8022.

When the screw 8021 is loosened, the tube slider 802 is advanceable and retractable relative to the needle slider 702. In this case, the distal end of the shaft portion 8021b of the screw 8021 is accommodated in the nut hole 8022. Alternatively, even if the distal end of the shaft portion 8021b of the screw 8021 protrudes from the nut hole 8022 to the needle slider 702 side, the distal end thereof is not in contact with the needle slider 702.

When the screw 8021 is tightened, the advancement and retraction of the tube slider 802 with respect to the needle slider 702 is restricted. In this case, the distal end of the shaft portion 8021b of the screw 8021 protrudes from the nut hole 8022 to the needle slider 702 side, and presses the outer peripheral surface of the needle slider 702 inwardly in the radial direction. As a result, in the outer peripheral surface of the needle slider 702, the side opposite to the side pressed by the screw 8021 in the radial direction is pressed against the inner peripheral surface of the tube slider 802 such that the movement of the tube slider 802 relative to the needle slider 702 in the longitudinal direction is restricted.

In the present embodiment, similar to the first embodiment, the puncture device 12 may be transitioned among the three states including the accommodation state (FIG. 14A), the transition state (FIG. 14B), and the protrusion state (FIG. 14C) by advancing and retracting the tube slider 802 in the longitudinal direction with respect to the needle slider 702.

By using the screw 8021, it is possible to restrict the relative movement between the tube slider 802 and the needle slider 702 more reliably than that according to the first embodiment.

Third Embodiment

Next, a third embodiment of the puncture device 1 will be described with reference to FIG. 15 and FIG. 16A to FIG. 16C. In the following description, the same configurations as those already described will be designated by the same reference signs, and duplicate descriptions will be omitted.

Figure 15:
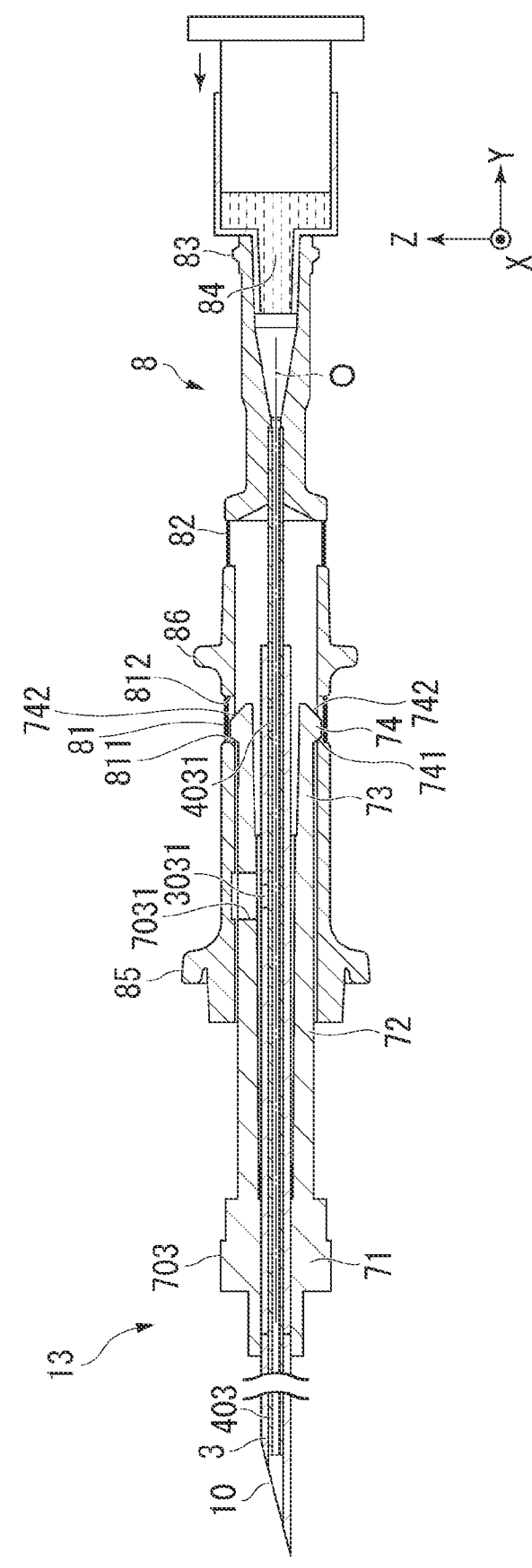
FIG. 15 is an example of a cross-sectional view showing a schematic configuration of a puncture device according to a third embodiment.
Figure 16A:
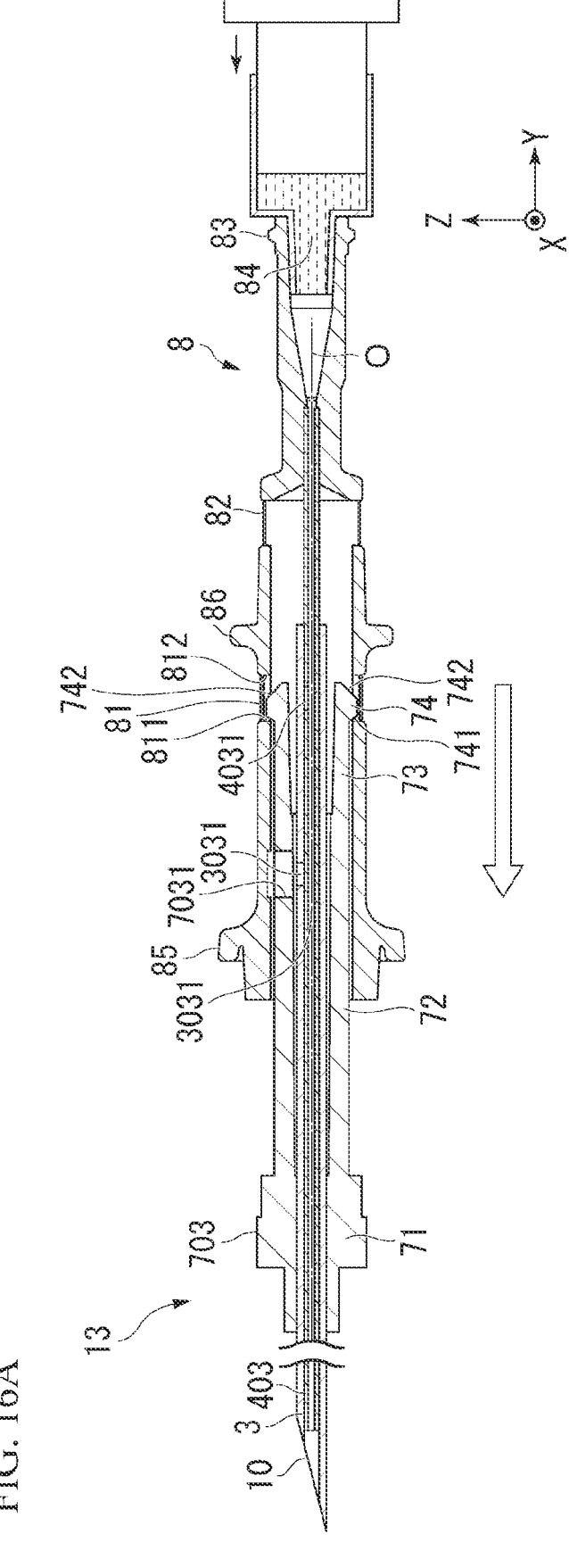
FIG. 16A is an example of a cross-sectional view showing an accommodation state in which a distal end of the protective tube is accommodated in the needle tube.
Figure 16B:
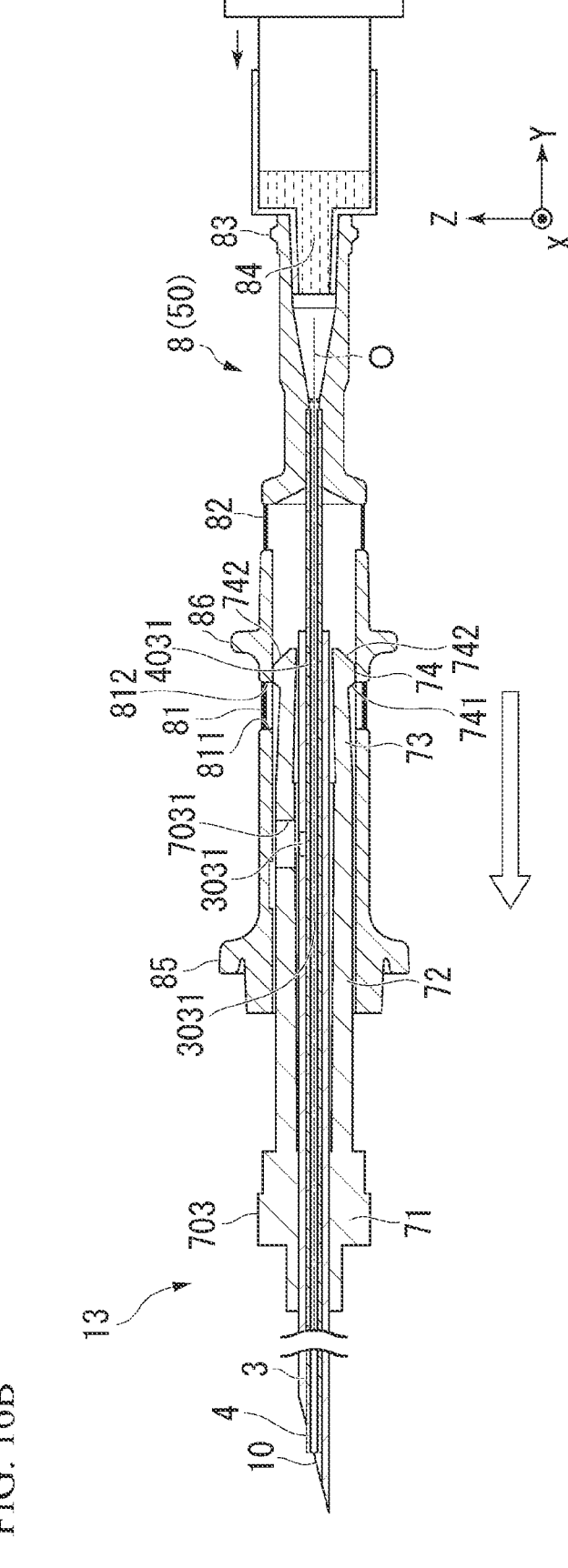
FIG. 16B is a view showing an example of a puncturing state in which the distal end of the protective tube is punctured from the needle tube.
Figure 16C:
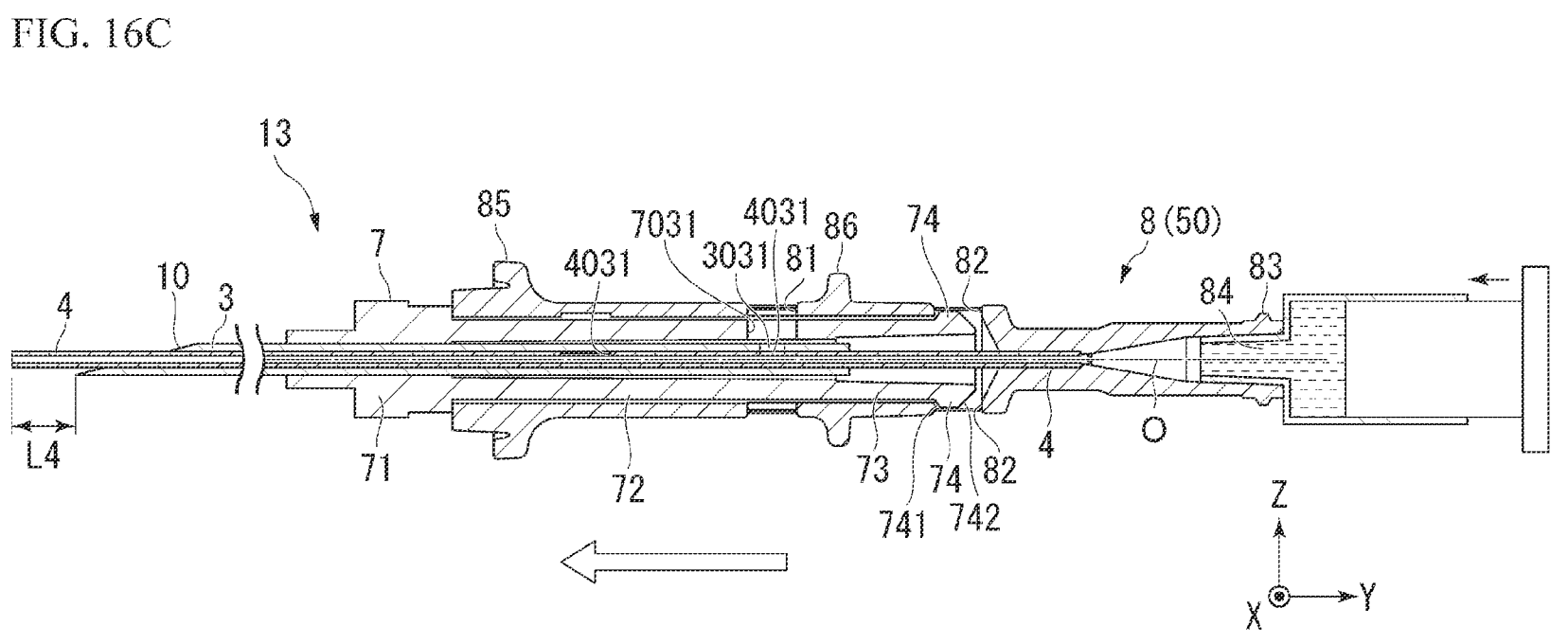

FIG. 15 is a cross-sectional view showing a schematic configuration of the puncture device in the third embodiment. FIG. 16A is a cross-sectional view showing an accommodation state in which the distal end of the protective tube 403 is accommodated in the needle tube 303. FIG. 16B is a view showing a puncturing state in which the distal end of the protective tube 403 is punctured from the needle tube 303. FIG. 16C is a cross-sectional view showing a protrusion state in which the distal end of the protective tube 403 protrudes from the needle tube 303.

The puncture device 13 according to the third embodiment is different from the first embodiment in the configurations of the needle slider 703, the protective tube 403 and the needle tube 303. The needle slider 703 according to the present embodiment as shown in FIG. 15 has a first opening 7031 penetrating in a direction perpendicular to the longitudinal direction. The first opening 7031 is provided, in particular, in the tube slider holder 72. The protective tube 403 has a second opening 4031 penetrating in a direction perpendicular to the central axis O. The needle tube 303 has a third opening 3031. The first opening 7031, the second opening 4031 and the third opening 3031 are arranged at positions where at least a part of the respective openings overlap each other in the longitudinal direction.

Here, as described above, the first locking portion 81 is an opening penetrating in the direction perpendicular to the central axis O. The opening of the first locking portion 81 is disposed at a position where at least a part thereof overlaps with the first opening 7031 and the second opening 4031 in the longitudinal direction.

As shown in FIG. 16C, when the puncture device 13 is in the protrusion state, the opening of the first locking portion 81 of the tube slider 8, the first opening 7031 of the needle slider 703, the second opening 4031 of the protective tube 403, and the third opening 3031 of the needle tube 303 are disposed such that at least a part thereof overlap each other in the longitudinal direction. That is, an opening is created through the outer surface of the tube slider 8 to the inner surface of the protective tube 403. That is, the inner space of the protective tube 403 communicates with the outside through the third opening 3031 of the needle tube 303, the first opening 7031 of the needle slider 703, and the opening of the first locking portion 81 of the tube slider 8. The surgeon may insert the guidewire from the outer surface of the tube slider 8 to the inner surface of the protective tube 403 or inject the contrast agent via the opening.

Similar to the first embodiment (FIG. 11: Step S4-1, Step S4-2), the surgeon injects the contrast agent from the injection port 84 into the protective tube 403 when the puncture device 13 is in the accommodation state (FIG. 16A). At this time, the second opening 4031 of the protective tube 4 is covered by the needle tube 303, the needle slider 703, and the tube slider 8 such that the contrast agent is introduced to the distal end of the protective tube 403.

Subsequently, the surgeon may proceed to Step S5 and Step S6 without performing step S4-3 of removing the syringe from the tube slider 8.

In Step S5, as shown in FIG. 16B, the surgeon advances the tube slider 8 with respect to the needle slider 703 to protrude the protective tube 403 from the needle tip 10 of the needle tube 3 as shown in FIG. 16C. Accordingly, the puncture device 13 is transitioned to the protrusion state, and an opening penetrating from the outer surface of the tube slider 8 to the inner surface of the protective tube 403 is created.

In Step S6, the guidewire 15 is inserted into the protective tube 403 through the opening created in Step S5 as shown in FIG. 16C.

By providing the first opening 7031 in the needle slider 702 and the second opening 4031 in the tube slider 802, it is not necessary to remove the syringe attached to the proximal end of the tube slider 8 when the guide wire 15 (FIG. 2) is inserted into the protective tube 403. Accordingly, the guide wire 15 may be used more smoothly than that in the first embodiment.

Although each embodiment of the present disclosure has been described above, the technical scope of the present invention is not limited to the above-described embodiment, and it is possible to change the combination of the constituent elements in each embodiment, or to add or delete various changes to each constituent element within a scope that does not depart from the spirit of the present invention.

1. A puncture device comprising: a sheath including a longitudinal axis; a needle tube disposed in the sheath to be advanceable and retractable along the longitudinal axis; a needle slider connected to the needle tube and configured to advance and retract the needle tube; an inner tube disposed in the sheath to be advanceable and retractable along the longitudinal axis, the inner tube including a lumen through which a guide wire is inserted to be advanceable and retractable along the longitudinal axis; a tube slider connected to the inner tube, supported to be movable in a direction along the longitudinal with respect to the needle slider, and configured to advance and retract the inner tube; and a locking portion configured to lock positions of the needle slider and the tube slider in the direction along the longitudinal axis in each of an accommodation state in which a distal end of the inner tube is accommodated in the needle tube and a protrusion state in which the distal end of the inner tube is protruded from the needle tube.

2. The puncture device according to the example 1, wherein:
the locking portion comprises a first locking portion and a second locking portion, the first locking portion is configured to lock the positions of the tube slider and the needle slider when the inner tube is in the accommodation state; and the second locking portion is configured to lock the positions of the tube slider and the needle slider when the inner tube is in the protrusion state.

3. The puncture device according to the example 2, wherein the first locking portion is formed of a concave portion provided in the tube slider and configured to engage with a claw provided in the needle slider; and the second locking portion is formed of a concave portion provided at a proximal end side of the first locking portion in the tube slider and configured to engage with the claw.

4. The puncture device according to the example 2, wherein the needle slider further comprises: a claw extending in a radial direction of the inner tube and configured to engage with the first locking portion and the second locking portion; and an arm including the claw and configured to change a position of the claw in the radial direction to release an engagement of the first locking portion, the second locking portion and the claw.

5. The puncture device according to the example 4, wherein the claw includes a first surface toward a distal end of the needle tube and a second surface toward a proximal end of the needle tube, and the first surface and the second surface are inclined with respect to radial direction.

6. The puncture device according to the example 4, wherein the arm includes an outer surface toward an outside in the radial direction and an inner surface toward an inside in the radial direction, and a distance between the inner surface at a proximal end of the arm and a central axis of the tube slider is larger than a distance between the inner surface at a distal end of the arm and the central axis of the tube slider.

7. The puncture device according to the example 1, wherein the tube slider is configured to attach an injection device for injecting a contrast medium into the inner tube; and the locking portion is configured to fix a position of the tube slider in the axial direction such that the inner tube enters the accommodation state in a state in which the injection device is attached to the tube slider.

8. The puncture device according to the example 1, wherein: the locking portion is a screw provided in the tube slider and extending in a radial direction of the tube slider, and the positions of the needle slider and the tube slider in the direction along the longitudinal axis are fixed by tightening the screw.

9. The puncture device according to the example 1, wherein: the locking portion includes an opening for fixing positions of the tube slider and the needle slider in the direction along the longitudinal axis when the inner tube is in the accommodating state, the tube slider includes a first opening penetrating in a direction perpendicular to the longitudinal axis, the inner tube includes a second opening penetrating in the direction perpendicular to the longitudinal axis, the needle tube incudes a third opening penetrating in the direction perpendicular to the longitudinal axis, and at least part of the opening, the first opening, the second opening, and the third opening are located to overlap in the direction along the longitudinal direction when the inner tube is in the accommodating state.

10. A puncture system comprising: a guide wire; and a puncture device, the puncture device comprising: a needle tube extending along a longitudinal axis and including a needle tip at a distal end thereof; a needle slider configured to control advancement and retraction of the needle tube; an inner tube inserted through the needle tube and through which the guide wire is insertable; a tube slider configured to control advancement and retraction of the inner tube; and a locking portion configured to lock positions of the needle slider and the tube slider in the direction along the longitudinal axis in each of an accommodation state in which a distal end of the inner tube is accommodated in the needle tube and a protrusion state in which the distal end of the inner tube is protruded from the needle tube.

11. The puncture system according to the example 10, further comprising: an injection device for injecting a contrast agent into the inner tube, wherein the locking portion is configured to fix the position of the tube slider such that the inner tube is in the accommodation state in the state in which the injection device is attached to the tube slider.

12. A usage method of a guide wire, the method comprising: forming a penetration hole by puncturing a needle tube from inside of a first lumen to a lumen wall of the first lumen and a lumen wall of a second lumen; disposing a needle tip of the needle tube in the second lumen; fixing positions of the needle tube and an inner tube in a state in which a distal end of the inner tube accommodated in the needle tube is at a proximal end side of the needle tip; injecting a contrast agent into the inner tube in a state in which the positions of the needle tube and the inner tube are fixed; protruding the inner tube from the needle tip after releasing the fixation of the positions of the needle tube and the inner tube; inserting a guide wire into the second lumen from a distal end of the inner tube; and indwelling the guide wire from the first lumen to the second lumen by removing the needle tube and the inner tube from the penetration hole.

13. The usage method of a guide wire according to the example 12, wherein: fix the positions of the needle tube and the inner tube by locking a tube slider for controlling advancement and retraction of the inner tube and a needle slider for controlling advancement and retraction of the needle tube in the state in which the distal end of the inner tube is at the proximal end side of the needle tip.

14. The usage method of a guide wire according to the example 12, wherein: fixing the positions of the needle tube and the inner tube by locking a tube slider for controlling advancement and retraction of the inner tube and a needle slider for controlling advancement and retraction of the needle tube in the state in which the inner tube is protruded from the needle tip.

15. The usage method of a guide wire according to the example 14, further comprising: moving the distal end of the inner tube toward the proximal end side of the needle tip by releasing fixation of the positions of the needle tip and the inner tube and moving the tube slider to the proximal end side with respect to the needle slider after fixing the positions of the needle tube and the inner tube in the state in which the inner tube is protruded from the needle tip.

16. An operation method of a puncture device, the method comprising: restricting a relative movement of a needle slider for controlling advancement and retraction of a needle tube and a tube slider for controlling advancement and retraction of an inner tube in a state in which a distal end of the inner tube is accommodated inside of the needle tube; protruding the needle tube from the distal end of the inner tube by advancing the tube slider with respect to the needle slider in the state in which the relative movement of the needle slider and the tube slider are restricted; and locking the needle slider and the tube slider to restrict the relative movement of the inner tube and the needle tube by further protruding the distal end of the inner tube from the needle tube.

17. The operation method of a puncture device according to the example 16, wherein restricting the relative movement of the needle slider and the tube slider by locking a claw provided in the needle slider and a locking portion provided in the tube slider.

18. The operation method of a puncture device according to the example 16, wherein: the locking portion includes a first locking portion and a second locking portion provided at a proximal end side of the tube slider than the first locking portion, restricting the relative movement of the needle slider and the tube slider by locking the claw and the first locking portion in the state in which the distal end of the inner tube is accommodated in the needle tube, and restricting the relative movement of the needle slider and the tube slider by locking the claw and the second locking portion in the state in which the distal end of the inner tube is protruded from the needle tube.

What is claimed is:

1. A puncture device comprising:

an elongate sheath, defining a longitudinal axis direction;

a needle tube, carried in the sheath, the needle tube configured to be movable in the longitudinal axis direction;

a needle slider, connected to the needle tube, the needle slider comprising a nail;

an inner tube, carried in the needle tube, the inner tube defining a lumen configured to receive a guide wire;

a tube slider, connected to the inner tube, the tube slider configured to support the inner tube such that the inner tube is movable in the longitudinal axis direction; and a locking member comprising a first concave portion and a second concave portion, wherein:

the second concave portion is disposed more proximally than the first concave portion;

the first concave portion and the second concave portion are configured to lock the needle slider relative to the tube slider in a first state and in a second state by engaging with the nail;

in the first state, a distal end of the inner tube is positioned in the needle tube by engaging the first concave with the nail; and in the second state, the distal end of the inner tube is positioned to protrude out from the needle tube by engaging the second concave with the nail.

2. The puncture device according to claim 1, wherein the needle slider further comprises:

a nail configured to engage with the first member and the second member, wherein the nail extends laterally or radially with respect to the inner tube; and an arm configured to change a lateral or radial position of the nail and configured to disengage the nail from the locking member.

3. The puncture device according to claim 2, wherein:

the nail includes a first surface and a second surface proximally located relative to the first surface;

the first surface is toward a distal end of the needle tube;

the second surface is toward a proximal end of the needle tube; and the first surface and the second surface are inclined along the longitudinal axis direction.

4. The puncture device according to claim 2, wherein:

the arm includes an inner surface located inside the needle slider; and a distance (D2) between the longitudinal and the inner surface at a proximal end of the arm is larger than a distance (D1) between the longitudinal axis and the inner surface at a distal end of the arm.

5. The puncture device according to claim 1, wherein:

the tube slider is configured to attach an injection device for injecting a contrast medium into the inner tube; and the locking member is configured to lock the needle slider relative to the tube slider such that the inner tube is in the first state when the tube slider attaches the injection device.

6. The puncture device according to claim 1, wherein:

the locking member includes a fourth opening, the fourth opening is configured to lock the needle slider in the second state;

the tube slider includes a first opening, the first opening is configured to penetrate in a direction perpendicular to the longitudinal axis;

the inner tube includes a second opening, the second opening is configured to penetrate in a direction perpendicular to the longitudinal axis;

the needle tube includes a third opening, the third opening is configured to penetrate in a direction perpendicular to the longitudinal axis; and the fourth opening, the first opening, the second opening, and the third opening are located such that at least a part of the fourth opening, the first opening, the second opening, and the third opening overlap along the longitudinal axis.

7. A puncture system comprising:

a guide wire; and a puncture device comprising:

a sheath configured to extend in a longitudinal axis direction;

a needle tube, carried in the sheath, the needle tube configured to be movable in the longitudinal axis direction;

a needle slider connected to the needle tube, the needle slider comprising a nail;

an inner tube carried in the needle tube, the inner tube defining a lumen configured to receive the guide wire;

a tube slider connected to the inner tube, the tube slider configured to support the inner tube such that the inner tube is movable in the longitudinal axis direction; and a locking member comprising a first concave portion and a second concave portion, wherein:

the second concave portion disposed more proximally than the first concave portion;

the first concave portion and the second concave portion are configured to lock the needle slider relative to the tube slider in a first state and in a second state by engaging with the nail;

in the first state, a distal end of the inner tube is positioned in the needle tube by engaging the first concave with the nail; and in the second state, the distal end of the inner tube is positioned to protrude from the needle tube by engaging the second concave with the nail.

8. The puncture system according to claim 7, further comprising:

an injection device for injecting a contrast medium into the inner tube, wherein the injection device is configured to attach to the tube slider.

9. A method for using a guide wire, the method comprising:

forming a first hole on a first lumen of a body by a needle tube;

forming a second hole on a second lumen of the body by the needle tube;

disposing a tip of the needle tube into the second lumen;

locking the needle tube relative to an inner tube in a locked state such that a tip of the inner tube is more proximal than the tip of the needle tube, the tip of the inner tube is configured to be positioned in the needle tube;

injecting a contrast medium into the inner tube with maintaining the locked state;

unlocking the locked state;

protruding the inner tube from the tip of the needle tube after unlocking the locked state;

inserting the guide wire into the second lumen from the tip of the inner tube; and leaving the guide wire extending from the first lumen to the second lumen by removing the needle tube and the inner tube from the first hole and the second hole.

10. The method according to claim 9, wherein:

the locking includes locking the needle tube relative to the inner tube including by locking a tube slider, configured to control advancing and retreating of the inner tube, and a needle slider, configured to control advancing and retreating of the needle tube, in a state that the tip of the inner tube is disposed distal than the tip of the needle tube.

11. The method according to claim 9, wherein:

the locking includes locking the needle tube relative to the inner tube including by locking a needle slider, configured to control advancing and retreating of the needle tube, relative to a tube slider, configured to control advancing and retreating of the inner tube, in a state that the inner tube protrudes from the tip of the needle tube.

12. The method according to claim 10, further comprising: moving the tip of the inner tube to a proximal end side relative to the tip of the needle tube by unlocking of the needle tube relative to the inner tube and moving the tube slider to a proximal end side relative to the needle slider after locking of the needle tube relative to the inner tube in a state in which the inner tube protrudes from the tip of the needle tube.

\* \* \* \* \*